US011963969B2

(12) United States Patent
Chang et al.

(10) Patent No.: US 11,963,969 B2
(45) Date of Patent: Apr. 23, 2024

(54) METHOD FOR PREVENTION OR TREATMENT OF AMYOTROPHIC LATERAL SCLEROSIS BY ADMINISTERING GASTRODIN

(71) Applicant: BUDDHIST TZU CHI MEDICAL FOUNDATION, Hualien (TW)

(72) Inventors: Chia-Yu Chang, Hualien (TW); Shinn-Zong Lin, Hualien (TW); Hsiao-Chien Ting, Hualien (TW); Hui-I Yang, Hualien (TW); Horng-Jyh Harn, Hualien (TW); Hong-Lin Su, Hualien (TW); Ching-Ann Liu, Hualien (TW); Yu-Shuan Chen, Hualien (TW); Tzyy-Wen Chiou, Hualien (TW); Tsung-Jung Ho, Hualien (TW)

(73) Assignee: BUDDHIST TZU CHI MEDICAL FOUNDATION, Hualien (TW)

( * ) Notice: Subject to any disclaimer, the term of this patent is extended or adjusted under 35 U.S.C. 154(b) by 0 days.

(21) Appl. No.: 17/932,781

(22) Filed: Sep. 16, 2022

(65) Prior Publication Data

US 2023/0263813 A1 Aug. 24, 2023

(30) Foreign Application Priority Data

Sep. 17, 2021 (TW) ................ 110134908

(51) Int. Cl.
*A61K 31/7034* (2006.01)
*A61K 9/00* (2006.01)
*A61K 31/428* (2006.01)
*A61P 25/28* (2006.01)

(52) U.S. Cl.
CPC ........ *A61K 31/7034* (2013.01); *A61K 9/0019* (2013.01); *A61K 31/428* (2013.01); *A61P 25/28* (2018.01)

(58) Field of Classification Search
CPC .............. A61K 31/7034; A61K 9/0019; A61K 31/428; A61P 25/28
USPC ........................................... 514/25
See application file for complete search history.

(56) References Cited

FOREIGN PATENT DOCUMENTS

CN 101322713 A * 12/2008
CN 101322713 A 12/2008

OTHER PUBLICATIONS

Machine Translation of CN101322713A, p. 2 (Year: 2008).*
Sawada, H. Clinical efficacy of edaravone for the treatment of amyotrophic lateral sclerosis. Expert Opinion on Pharmacotherapy, 18(7), 735-738. https://doi.org/10.1080/14656566.2017.1319937 (Year: 2017).*
Kuraszkiewicz et al. (2020). Potential Preventive Strategies for Amyotrophic Lateral Sclerosis. Frontiers in Neuroscience, 14. https://doi.org/10.3389/fnins.2020.00428 (Year: 2020).*
Jiang et al., "Pharmacological Effect and Mechanism of Gastrodin on ALS Cell Model", Traditional Chinese Drug Research & Clinical Pharmacology, Nov. 2017, vol. 28 No. 6, 5 pages provided; Cited in Office Action issued in Taiwanese Application; with English Abstract.

* cited by examiner

*Primary Examiner* — Yih-Horng Shiao
*Assistant Examiner* — Yancey Lee
(74) *Attorney, Agent, or Firm* — HSML P.C.

(57) ABSTRACT

Provided is a pharmaceutical composition including gastrodin and a use thereof for the prevention or the treatment of amyotrophic lateral sclerosis. The pharmaceutical composition is effective in reducing neuronal axon degeneration and neurofibromin accumulation, improving symptoms of amyotrophic lateral sclerosis and extending life of patients of amyotrophic lateral sclerosis.

9 Claims, 27 Drawing Sheets
(18 of 27 Drawing Sheet(s) Filed in Color)
Specification includes a Sequence Listing.

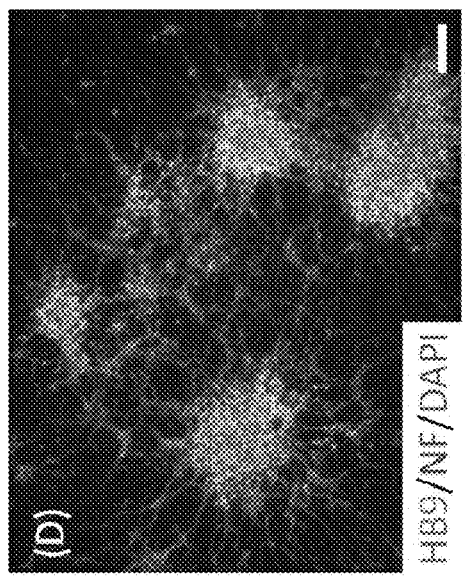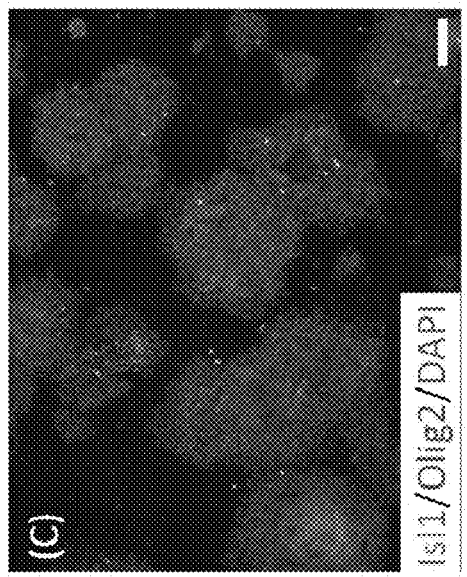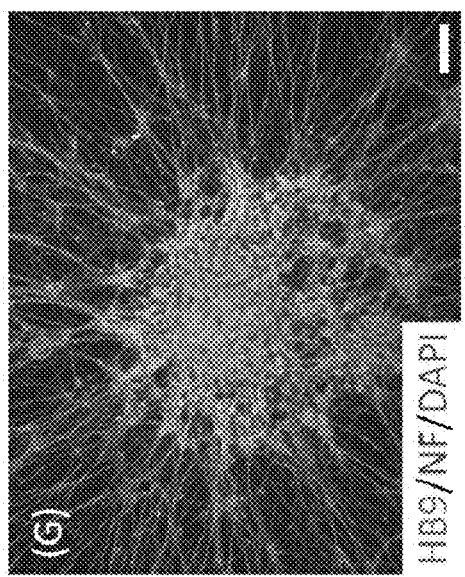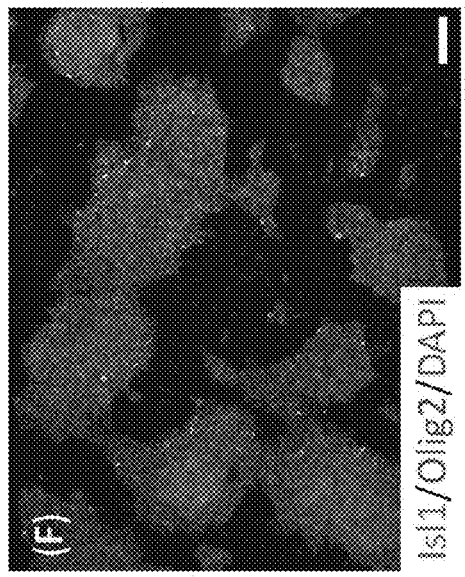
FIG. 2B  FIG. 2C  FIG. 2D  FIG. 2E  FIG. 2F  FIG. 2G

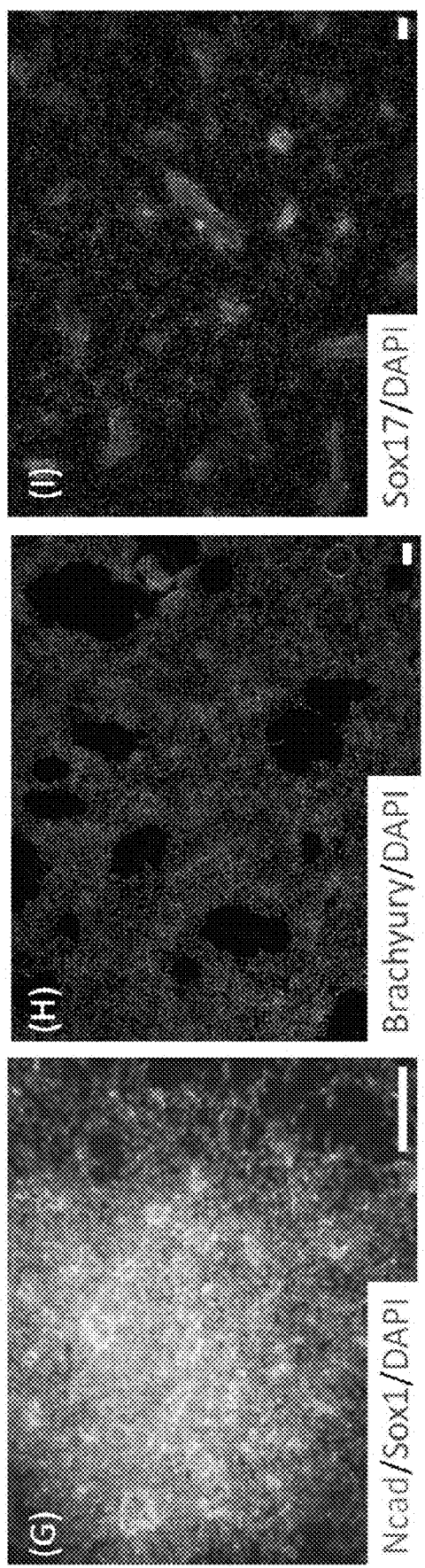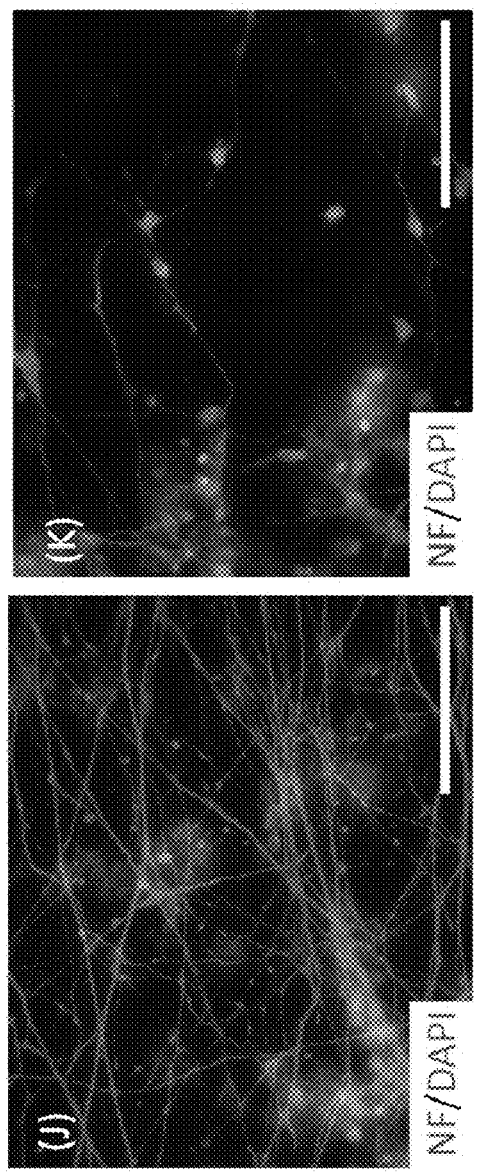
FIG. 6I
FIG. 6K
FIG. 6H
FIG. 6J
FIG. 6G

SEQUENCE LISTING

```
Sequence total quantity: 2
SEQ ID NO: 1            moltype = DNA  length = 23
FEATURE                 Location/Qualifiers
source                  1..23
                        mol_type = other DNA
                        organism = synthetic construct
SEQUENCE: 1
agtcacattg cgcaagtctc caa                                            23

SEQ ID NO: 2            moltype = DNA  length = 23
FEATURE                 Location/Qualifiers
source                  1..23
                        mol_type = other DNA
                        organism = synthetic construct
SEQUENCE: 2
agtcacattg cccaagtctc caa                                            23
```

METHOD FOR PREVENTION OR TREATMENT OF AMYOTROPHIC LATERAL SCLEROSIS BY ADMINISTERING GASTRODIN

TECHNICAL FIELD

The disclosure relates generally to a method for prevention or treatment of amyotrophic lateral sclerosis (ALS), especially to a method for preventing or treating ALS by administering gastrodin to a subject. The disclosure also relates to a pharmaceutical composition for use in prevention or treatment of ALS in a subject in need thereof.

SEQUENCE LISTING

The present application is being filed along with a Sequence Listing in electronic format. The Sequence Listing is provided as a file entitled 210804US-Sequence Listing.XML, created on Nov. 20, 2022, which is 2.68 kb in size. The information in the electronic format of Sequence Listing is incorporated herein by reference in its entirety.

BACKGROUND

Amyotrophic lateral sclerosis (ALS) is a neurodegenerative disease with a worldwide incidence rate about $5/100,000$. The motor neurons in the spinal cord and brain of a patient with ALS degenerate gradually, which in turn results in symptoms of muscle atrophy, difficulty in action, difficulty in swallowing, respiratory failure, and the like. The early signs of ALS include fasciculation, cramp, stiffness, or mild weakness, etc. Dysphonia is also a symptom which may occur at the early stage and can further develop into difficulty in chewing or swallowing over time. As the disease progresses, muscles gradually become weak, and the limbs become thinner and weaker due to muscle atrophy. Finally, the patients may not be able to walk independently, may need to rely on wheelchairs, lose the function of the upper limbs gradually, and need assistance in their daily life routine. In general, a patient with ALS may result in death from respiratory failure usually within 2 to years after incidence.

Based on the onset signs at an earlier stage, clinical symptoms and genetic identification results, ALS are classified into different types. More than 90% of the patients with ALS have no obvious familial association and related known genetic mutation. They are classified into sporadic ALS with an average onset in their 50s and 60s. Only about 5% to 10% of the patients with ALS have obvious genetic association and genetic characteristics. They are classified into hereditary ALS with an average onset in their 40s and 50s. In addition, a rare form disease with an onset in childhood or teens is so-called juvenile ALS. Some families of ALS patients may have symptoms of frontotemporal dementia and Parkinson's disease, which affect a person's personality, behavior, and language ability when it occurs.

Currently, two categories of medicaments are approved by the FDA for clinical treatment of ALS: riluzole, a glutamate antagonist, and edaravone, an antioxidant. Riluzole in combination with creatine, vitamin E, vitamin C is the current standard therapy, which can alleviate the symptoms of ALS and extend the life of the patient by about 2 to 3 months, but it does not cure or delay progression of ALS. Edaravone can alleviate the degeneration rate of motor ability, but there is no significant data on the prolongation of life.

Gastrodin is one of the main ingredients of the traditional Chinese medicine *Gastrodia elata*, which is a small glucoside molecule. *Gastrodia data* is a traditional Chinese medicine which has been used for at least a thousand years in the treatment of dizziness, headache, seizures and cramp; the methanol extract of which has also been used for the treatment of Alzheimer's amyloid peptide deposition, Parkinson's disease, ischemic stroke, anxiety and depression in an animal or cell model. However, no report has shown the therapeutic effect of gastrodin on motor neuron diseases or neuromuscular diseases, yet.

Currently, the clinical medicament of riluzole for ALS can only achieve an average life extension of the patients by about 2 to 3 months. Thus, there is an urgent need in clinical application for development of new medicaments or a new drug combined with the existing medicaments to treat ALS effectively.

SUMMARY

The disclosure provides a pharmaceutical composition used for the prevention or the treatment of amyotrophic lateral sclerosis, wherein the pharmaceutical composition comprises a therapeutically effective dose of gastrodin and a pharmaceutically acceptable carrier. The disclosure also provides a use of the pharmaceutical composition in manufacture of a medicament for the prevention or the treatment of amyotrophic lateral sclerosis in a subject in need thereof.

In an embodiment, the therapeutically effective dose of gastrodin is in a range from about 1 mg/kg body weight to about 1,000 mg/kg body weight per day. For example, the gastrodin is administered to the subject at a therapeutically effective dose of about 1 mg/kg/day to about 1,000 mg/kg/day, about 5 mg/kg/day to about 750 mg/kg/day, about 10 mg/kg/day to about 500 mg/kg/day, about 15 mg/kg/day to about 400 mg/kg/day, about 20 mg/kg/day to about 300 mg/kg/day, or about 30 mg/kg/day to about 250 mg/kg/day.

In an embodiment, the gastrodin is administered to a subject for a period of 1 month to 3 years; for example, the gastrodin is administered for 1 month, 2 months, 3 months, 6 months, 10 months, 1 year, 2 years, or 3 years.

In an embodiment, the gastrodin has at least one of the following effects on the subject: improvement in axon growth of neurons, decrease in accumulation of neurofilaments, and recovery of nerve electrophysiological function.

In an embodiment, the pharmaceutical composition is administered to the subject by at least one route selected from the group consisting of corticospinal, intrathecal, intracerebral, intravenous, intraperitoneal, and subcutaneous injection.

In an embodiment, the subject has hereditary amyotrophic lateral sclerosis or sporadic amyotrophic lateral sclerosis.

In an embodiment, the superoxide dismutase 1 gene of the subject contains at least one amino acid mutation; for example, the subject is an $SOD1^{G85R}$ mutant or $SOD1^{D90A}$ mutant.

The pharmaceutical composition of the disclosure may comprise gastrodin alone as the active ingredient to prevent or treat amyotrophic lateral sclerosis. In other words, the gastrodin is the only active ingredient in the composition to prevent or treat amyotrophic lateral sclerosis. In this example, the disclosure provides a safe and effective method for the prevention or the treatment of amyotrophic lateral sclerosis by using gastrodin alone as the active ingredient.

Alternatively, in another example, the pharmaceutical composition of the disclosure can be administered in combination with another active ingredient to a subject, unless the efficacy of the disclosure is suppressed. The gastrodin and other active ingredients can be provided in a single composition or in separated compositions.

In an embodiment, in the use provided in the disclosure, administration of at least one additional therapy for amyotrophic lateral sclerosis to the subject is further comprised. In an embodiment, the administration of gastrodin can be combined with any suitable therapy for amyotrophic lateral sclerosis. In an embodiment, the additional therapy for amyotrophic lateral sclerosis is administration of riluzole, edaravone, or creatine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to understand the disclosure in more detail, the following description has been made in reference to the figures below.

FIGS. 2B to 2D are photographs of the motor neurons differentiated from SOD1$^{G85R}$ iPSCs, respectively.

FIGS. 2E to 2G are photographs of the motor neurons differentiated from SOD1$^{G85G}$ iPSCs.

FIGS. 6G to 6I show the expression profiles of the neurorctodermal markers Ncad and Sox1, the mesodermal marker Brachyury and the endodermal marker Sox17 of the sALS iPSC cell line, respectively.

FIGS. 6J and 6K show the spherical nerve fiber beads in the motor neurons differentiated from the sALS iPSCs.

DETAILED DESCRIPTION OF THE EMBODIMENTS

Figure 1A:
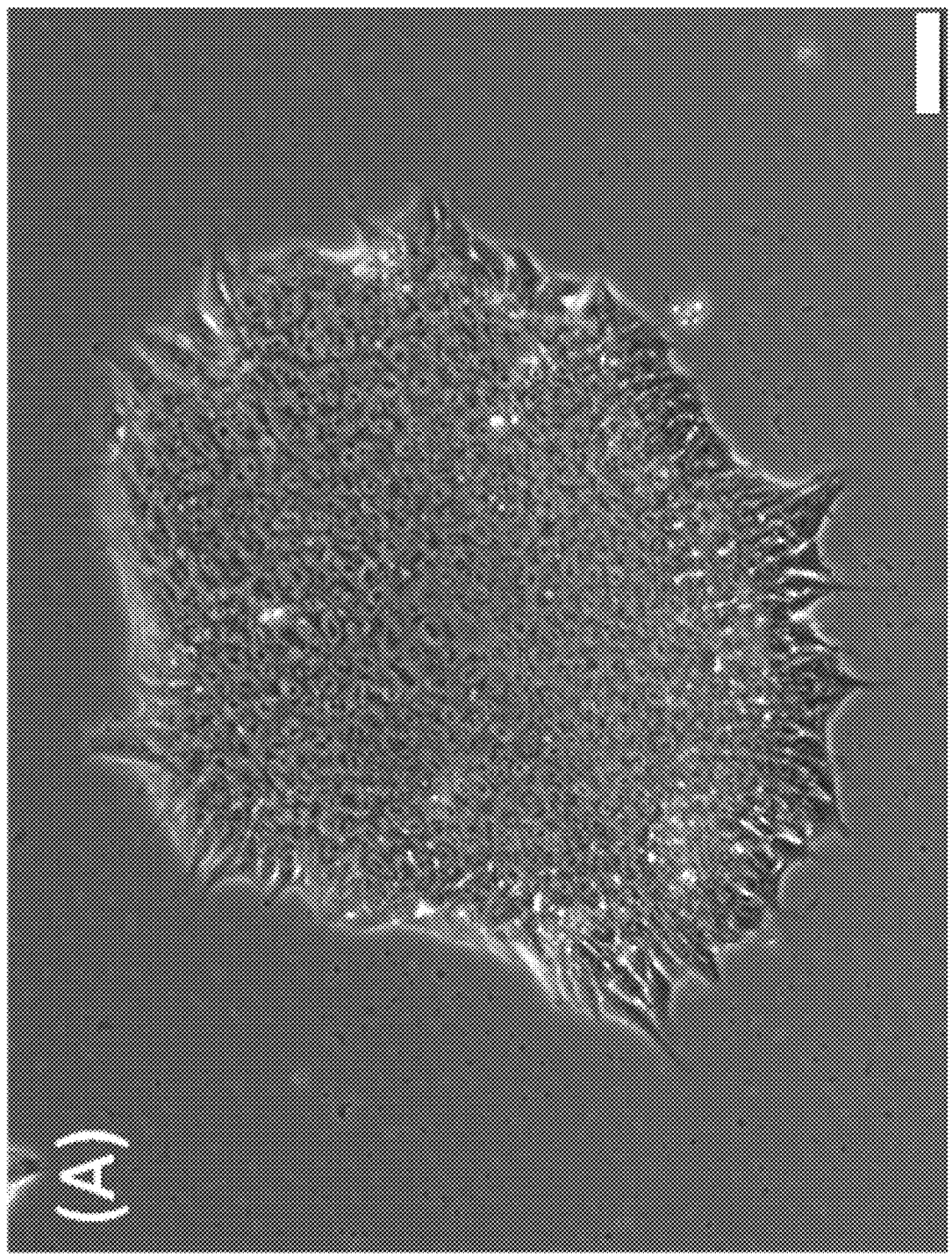
FIG. 1A is an iPS cell line established by reprogramming technique from peripheral blood mononuclear cells of a patient with ALS.

Referencing to figures which constitute a portion of the description of examples, the embodiments for implementation of the disclosure are illustrated. It should be understood that other examples can be used, and alternation on structures also can be made without departing from the scope of the disclosure.

Unless otherwise stated herein, the singular form "a," "an" and "the" used in this description and the attached claims should be considered to encompass the singular and the plural forms, unless it is otherwise stated or obviously contradictory to the context.

The term "about" used herein refers to be approximate or close to, and in the context of a value or range recited refers to ±5% of the value. In an example, the term "about" may comprise traditional rounding based on the significant number of the value. In addition, the phrase "about x to y" comprises "about x to about y."

Unless otherwise stated herein, the term "or" used in this description and the attached claims typically comprises the use in the meaning of "and/or." As used herein and unless otherwise stated, the conjunction "and" is intended to be inclusive, and the conjunction "or" is not intended to be exclusive. For example, the phrase "or alternatively" is intended to be exclusive.

Unless otherwise stated, the terms "comprise," "have," "include" and "contain" should be considered to be open forms (i.e., means "includes but not limited to").

Unless otherwise stated herein, the statement of a value range is only for the purpose of abbreviation of all single values falling into the range, and each single value is incorporated in the specification as if it is stated individually herein.

Unless otherwise stated herein or contradictory to the context, all methods described herein can be performed in any appropriate order. Unless otherwise required, the use of any and all examples or exemplary words (e.g., "such as" and "for example") is only for setting forth of the disclosure rather than forming restriction to the scope of the disclosure.

The disclosure provides a method for the prevention or the treatment of a subject with amyotrophic lateral sclerosis (ALS), comprising administering a therapeutically effective dose of gastrodin to the subject, wherein the subject may be an individual suffering from amyotrophic lateral sclerosis.

The disclosure provides a use of a pharmaceutical composition for preparation of a medicament for the prevention or the treatment of ALS in a subject in need thereof, wherein the pharmaceutical composition comprises a therapeutically effective dose of gastrodin and a pharmaceutically acceptable carrier.

As used herein, the term "preventing" or "prevention" is defined as a probability for elimination or reduction of the occurrence of one or more symptom(s) of a disease or disorder. For example, the composition described herein can be used for preventing the axonal degeneration of neurons or reducing accumulation of neurofilament.

As used herein, the term "treating" or "treatment" is directed to the administration of an effective dose of gastrodin to a subject in need thereof to cure, relieve, treat, improve or prevent the disease, the symptoms thereof or the risk to develop the disease. The subject can be identified by a medical care professional based on the results from any appropriate diagnostic method.

As used herein, the term "therapeutically effective dose" refers to a treatment dosage which is sufficient to result in preventing the development, recurrence or onset of ALS and one or more symptoms thereof, enhancing or improving the prevention effect of another therapy, reducing severity and phases of ALS, improving one or more symptoms of ALS, preventing progression of ALS, and/or enhancing or improving the therapeutic effect of another therapy.

As used herein, the term "subject" is any organism in need of treatment and/or prevention for ALS. In one example, the subject is a mammal including but not limited to human, a domesticated animal (e.g., a dog, a cat, a horse), a livestock (e.g., a cattle, a pig) and a wild animal.

In some examples of the disclosure, the pharmaceutical composition of the disclosure comprises gastrodin and a pharmaceutically acceptable carrier. In an example, the pharmaceutically acceptable carrier includes but is not limited to a filler, a binder, a preservative, a disintegrating agent, a lubricant, a suspending agent, a wetting agent, a solvent, a surfactant, an acid, a humectant, polyethylene glycol (PEG), an alkylene glycol, sebacic acid, dimethyl sulfoxide, ethanol, and any combination thereof.

The features and efficacies of the disclosure will be further illustrated by embodiments which are not intended to restrict the scope of the disclosure.

EXAMPLES

Study Methods and Materials:

(1) Amyotrophic Lateral Sclerosis Model Mice

B6SJL-Tg (SOD1*G93A) 1Gur/J transgenic mice are commonly used as the models for the first-line test of amyotrophic lateral sclerosis, which over-express human silence superoxide dismutase 1 (SOD1) gene G93A mutant in a transgenic mode and exhibit typical dyskinesia and pathological features of amyotrophic lateral sclerosis. The mice began to develop limb onsets in 80 to 90 days after birth, gradually lose ability to walk, and muscle weakness and atrophy started spreading to the upper parts of body. Most of their voluntary muscles became paralyzed and death after 110 to 120 days due to gradual loss of chewing ability and respiratory failure. The pathological characteristics include symptoms of amyotrophic lateral sclerosis such as muscular dystrophy, synaptic loss of motor neurons, degeneration and death of motor neurons, dismantling of the neuromuscular junction, etc.

(2) Motor Neural Differentiation of Induced Pluripotent Stem Cells

After the discovery of induced pluripotent stem cells (iPSCs) in cell transplantation therapy and in vitro disease simulation established by Professor Shinya Yamanaka in 2006 and 2007, the application of cell transplantation therapy and in vitro disease simulation has been highly anticipated, and the technique is used in reprogramming, which is a conversion of a downstream mature differentiated cell into early stage embryonic stem cells. These cells possess a high number of proliferative potential and enhanced differentiation into all types of adult cells in vitro. For the application of iPSCs in ALS, several international research teams have studied the conversion of somatic cells from patients into motor neurons and glia cells and the symptoms of the disease, and various gene mutations causing sporadic ALS and signs in neurons and glia cells have been discovered. For example, Professor Su-Chun Zhang disclosed in 2014 publication that the SOD1 gene mutant motor neurons would exhibit the typical sign of nerve fiber beads (e.g., $SOD1^{D90A}$ motor neurons would cause the abnormal aggregation of neurofilaments). Other investigators also discovered the signs such as impaired transportation of mitochondria and nucleus membrane. Recent studies have also discovered that glia cells differentiated from ALS iPSCs, including starshaped glial cells and oligodendritic cells, also exhibit symptoms such as protein aggregation and accumulation, leading to neurodegeneration which compromises the function and growth of neurons, and even with motor neuron impairment.

Figure 2A:
FIG. 2A is a schematic flow diagram of a method for the motor neural differentiation from induced pluripotent stem cells.
Figure 2H:
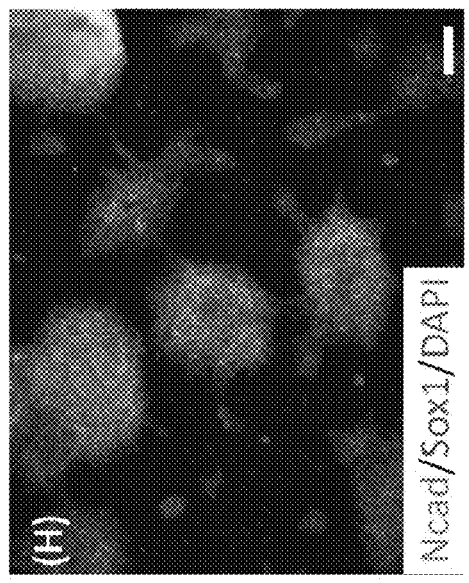
FIGS. 2H to 2J are photographs of motor neurons differentiated from SOD1$^{D90A}$ iPSCs.
Figure 2I:
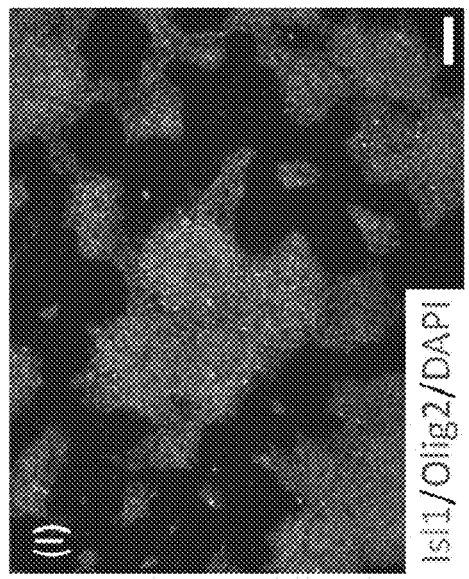
Figure 2J:
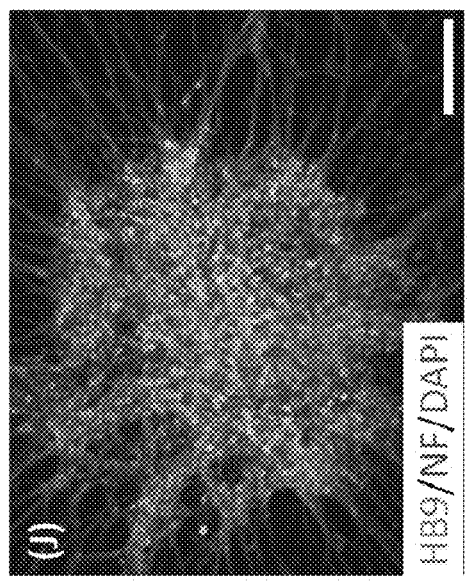
Figure 2K:
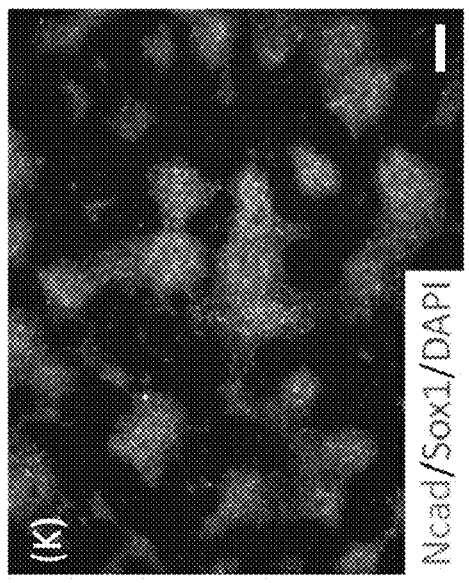
FIGS. 2K to 2M are photographs of motor neurons differentiated from SOD1$^{D90D}$ iPSCs.
Figure 2L:
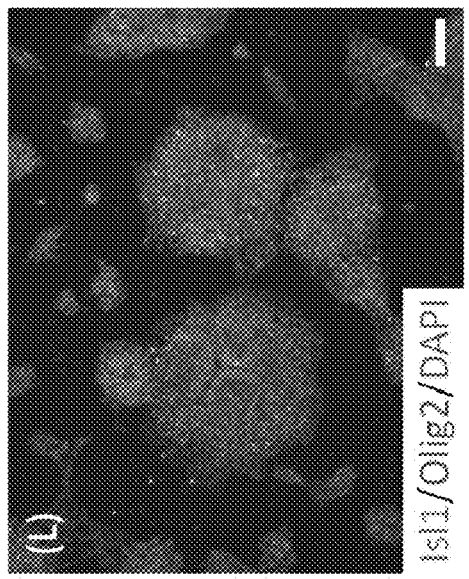
Figure 2M:
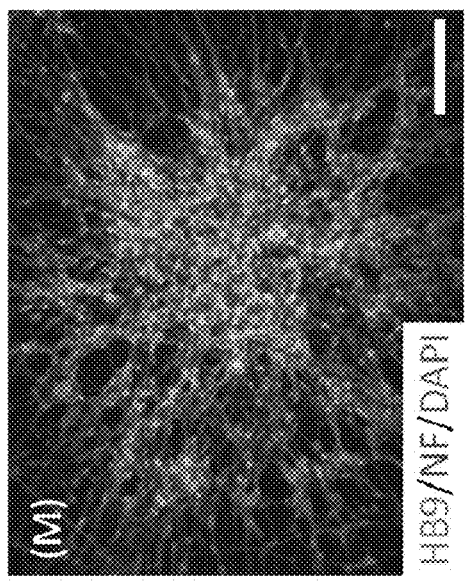
Figure 2N:
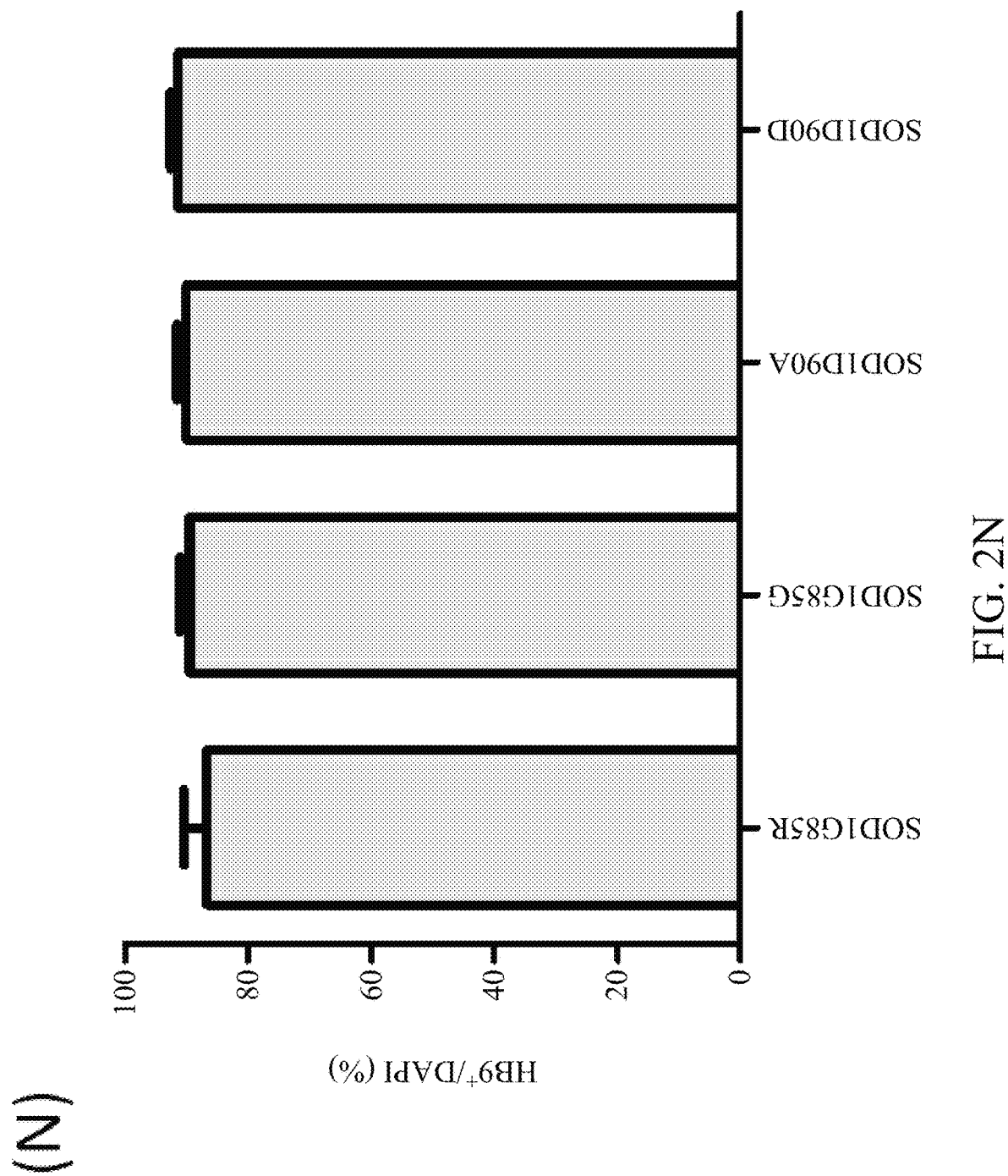
FIG. 2N shows the HB9 expression quantity of the motor neurons differentiated from each iPSC line.

The operation procedure for the induced differentiation of human induced pluripotent stem cells (hPSCs) into motor progenitor cells was performed in four stages in this disclosure (see FIG. 2A):

Stage I. hPSCs Induced into a Serum-Free Embryoid Body (SFEB) Aggregated Sphere Structure to Facilitate Differentiation This stage was the initial step of the differentiation. Firstly, subcultured hPSCs were harvested, and growth factor-free hPSC medium (Essential 6 or StemLite) was added to the cell suspension. The cell suspension was pipetted on a 6 cm$^2$ low attachment culture slide and incubated for 1 day, allowing the hPSCs to form aggregates as spherical embryoid bodies.

Stage II. Neuroepithelial Differentiation Induced by the Neural Stem Cell Induction Mode of CHIR99021, SB431542 and FGF-2 (Abbreviated as CHSF)

The aggregated embryoid body formed by the hPSCs was transferred into a 15 mL centrifuge tube, and the supernatant was removed by a pipette after cells settled. The residual embryoid body medium was removed via rinsing with 4 to 8 mL of neural induction medium (NI medium, Gibco), and the cells were allowed to settle. After the supernatant was pipetted carefully, a neural induction medium containing fibroblast growth factor 2 (FGF-2) (10 ng/mL), TGF-β/Smad inhibitor (SB431542) (2 µM) and GSK-3 inhibitor (CHIR99021) (3 µM) were added, and the culture was incubated for 3 days.

Stage III. Formation of Neural Stem Cells

After confirming that neuroepithelial structures occurred in the embryoid body, the neural induction medium was replaced with a neurobasal medium (NB medium, Gibco). The neuroepithelial from the previous stage was cultured in suspension, and a smoothened agonist (SAG) (3 µM), retinoic acid (RA) (3 µM) and LDN193189 (0.2 µM) were added continuously to promote motor neuronal differentiation. In this stage, the medium was changed every 1 to 3 days for at least 15 days, and from Day 7, the embryoid body was placed in a stirred bioreactor in which it was cultured and agitated at 90 rpm.

Stage IV. Adhesion and Identification of Neural Tube-Like Rosettes

Neural progenitor cells were adhered on 1 to 1.3% Matrigel® matrix gel or a culture slide coated with laminin-511. Structures of neural tube-like rosettes were observed, and the proportion of motor progenitor cells was identified on Day 15 of the differentiation.

(3) Dosing to the Cells

The gastrodin was diluted with dimethyl sulfoxide (DMSO) to 10 mM, added to the motor neurons differentiated at Day 25, Day 35 and Day 45 at a dosage ratio of 1:1,000, and cultured for 72 hours (hrs) for various assays.

(4) Assessment of Symptoms of Motor Neuron Disease a. Immunofluorescent Staining Assay A 4-well culture slide with a glass cover placed thereon was coated with 1% Geltrex®, placed at 37° C. for at least 3 to 4 hrs, washed with phosphate buffered saline (PBS) once after removal of the Geltrex®, and soaked in a culture medium until use. The embryoid bodies were dissociated with enzymes or mechanical force into smaller pieces, seeded on the 4-well culture slide, and cultured for 3 days (optionally for a longer period). After the cells adhered and extended outwards to present rosettes with a neural tube-like or a neuronal morphology, the immunofluorescent staining was then performed.

For the immunofluorescent staining, the medium was firstly removed, and then the cells were washed with PBS at room temperature twice. Next, 200 µL of 4% paraformaldehyde was added to the cells, and the mixture was reacted at room temperature for 5 to 15 min to fix the cells. The cells were washed with PBS for 3 times for 5 min each, and 200 µL of 99% methanol or 0.3% Triton® was added. The mixture was incubated for 5 to 15 min at 4° C., and the liquid was removed after permeabilization. The methanol, if used for fixation, was volatilized out. Then, the mixture was washed with PBS for 3 times (each for 5 min), and 200 µL of 5% horse serum was added at room temperature for at least 1 hr for blocking. Then, the serum was removed, and a primary antibody (prepared in 3% horse serum at a concentration suggested by the manufacturer of the antibody) was added. The primary antibody was removed after conjugation for 16 hrs, followed by washing with PBS and Tween® 20 (abbreviated as PBST hereinafter) for 3 times for 5 min each, and a secondary antibody (prepared in PBS at a concentration of 1:500) was added. The secondary antibody was kept in dark for 1 hour at room temperature. After removal of the secondary antibody, the mixture was washed 3 times with PBST for 5 min each.

Thereafter, the cells were labeled via nuclear staining by adding 200 µL of 4',6-diamidino-2-phenylindole (DAPI) (1 µg/mL), reacting in dark for 5 to 15 min at room temperature, removing DAPI, washing with PBST twice for 5 min each, removing PBST, adding PBS to maintain the cell moisture, lifting the glass coverslip with a needle tip, reversing the glass coverslip to the side with 50% glycerol or a mounting gel, storing in dark at 4° C., observing with a fluorescence microscope or a confocal microscope and photographing, and subsequently quantifying the numbers of neurofilaments and nerve fiber beads using an OLYMPUS cellSens Dimension Desktop 2.3 software.

b. Calcium Ion Image Analysis

Cells were seeded on a Geltrex®-coated round glass slide having a diameter of 10 mm, and cultured in a neurobasal medium supplemented with RevitaCell® and compound E for 3 days. 1 µM calcium fluorescent probe Fluo-4 solution was prepared in a physiological buffer containing 30 mM NaCl, 5 mM KCl, 2 mM CaCl$_2$, 2 mM MgCl$_2$, 10 mM glucose and 10 mM HEPES, and the glass slide on which the cells were seeded was transferred into the 1 µM Fluo-4 solution and cultured at 37° C. for 4 min. The glass slide was transferred into a physiological buffer and cultured at 37° C. for 20 min. The glass slide with cells seeded thereon was transferred into a calcium imaging chamber for imaging under perfusion.

Images were taken under perfusion with a physiological buffer for 30 seconds, then under perfusion with 60 mM KCl for 1 min, and then under perfusion with a physiological buffer for 5 min. Next, images were taken under perfusion with 1 mM glutamate for 1 min, and then under perfusion with a physiological buffer for 5 min. Images were captured with a microscope (Nikon ECLIPSE Ti2-E) and analyzed using NIS-Elements AR software.

(5) Dosing to Mice

Sixty days after birth, the ALS model mice (B6SJL-Tg (SOD1*G93A) 1Gur/J) were administered with gastrodin cycles once every 30 days as a single cycle, and 5 intraperitoneal injection of gastrodin was administered (with one day interval between every two intraperitoneal injections) at the first 10 days. No injection was administered during the subsequent 20 days. A total of two cycles of dosing may be performed until 120 days after birth. The ALS model mice showed onset of symptoms at about 90 days of age; therefore, the evaluation of disease indexes may be performed via a method for evaluation and analysis of hindlimb coordination, i.e., Basso Beattie Bresnahan (BBB) rating score. Further, as the ALS model mice resulted in death gradually at about 110 to 120 days after birth, the survival time was used for evaluating the therapeutic effect of the drug.

Example 1: Establishment and Identification of SOD1$^{G85R}$ ALS iPSCs

Figure 1B:
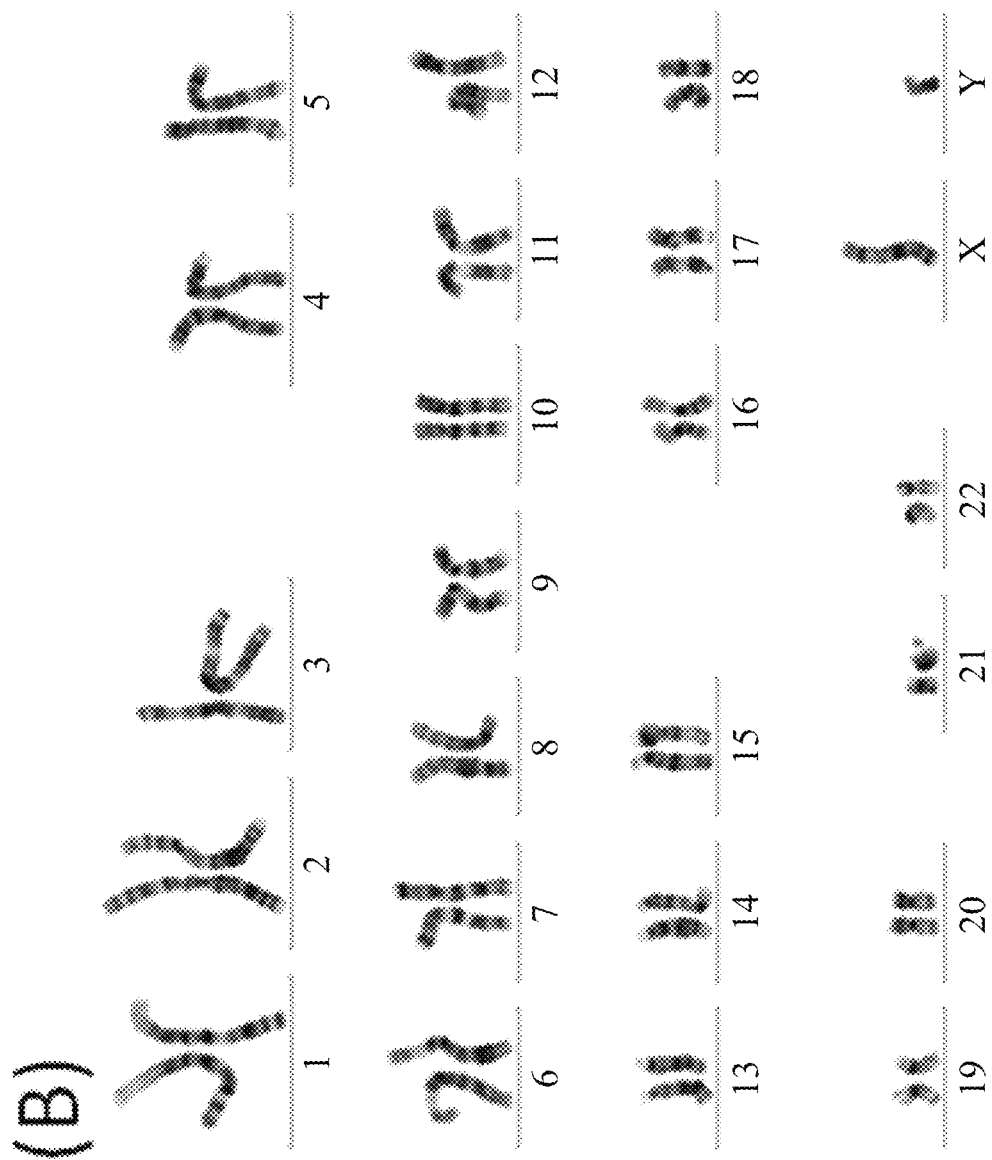
FIG. 1B shows the chromosome karyogram thereof.

The iPS cell line established via the reprogramming technique from peripheral blood mononuclear cells of a patient with ALS named as SOD1$^{G85R}$ iPSCs was shown in FIG. 1A. It was confirmed by an immunofluorescent staining assay that the cell line expressed iPSCs-specific cell markers, i.e., Oct4, Nanog, Sox2 and SSEA4 (FIGS. 1D to 1G). Further, the established iPSCs were tested by the immunofluorescent staining assay to have the ability to differentiate into three types of dermal layers (FIGS. 1H to 1J; neurorctodermal markers: Sox1 and Ncad; mesodermal marker: Brachyury; endodermal marker: Sox17). In addition, as shown in FIG. 1B, the established iPSCs have normal chromosome karyotypes.

Figure 1C:
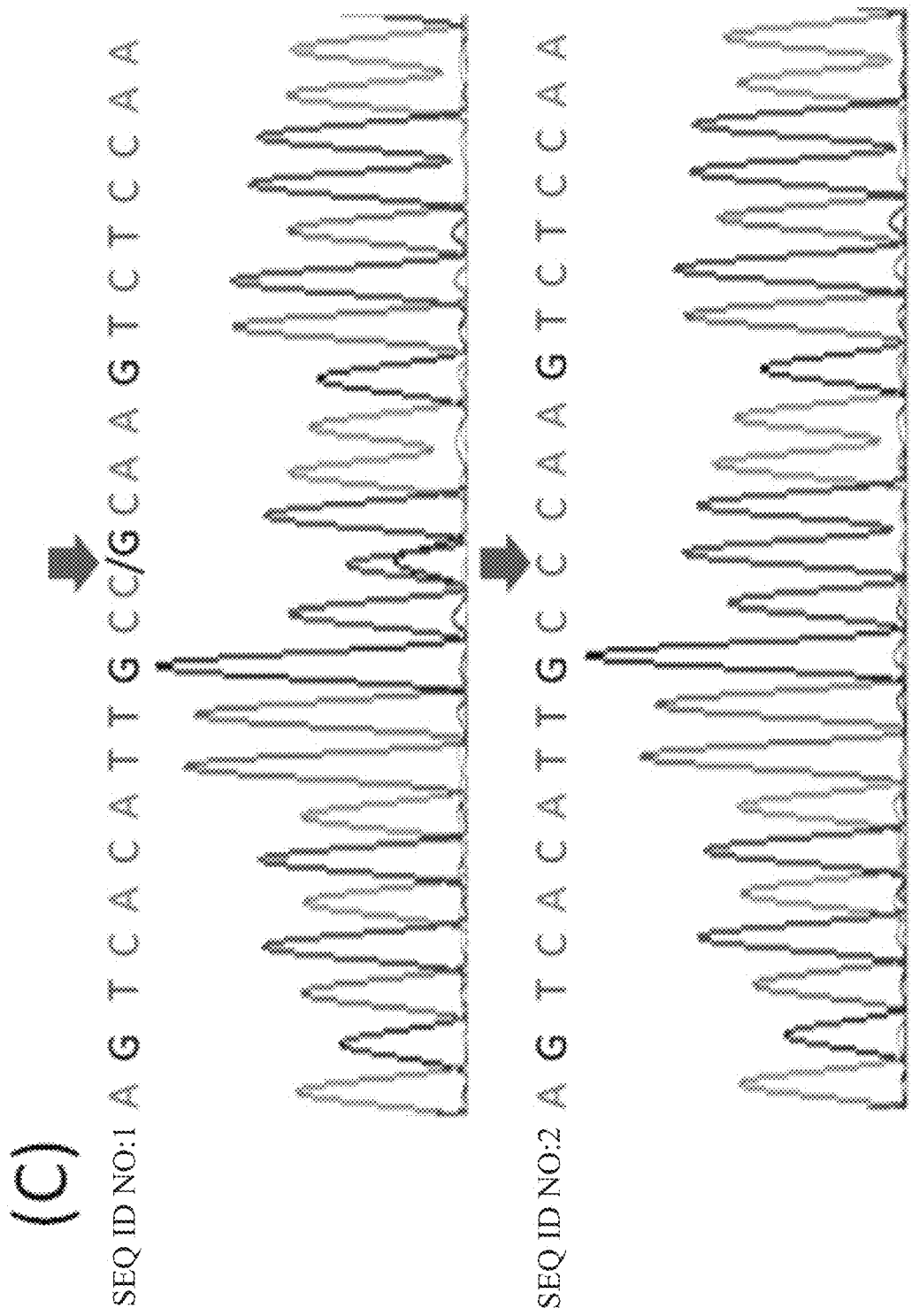
FIG. 1C shows a part of the sequencing result (SEQ ID NO: 1) of the SOD1 gene in the ALS iPS cell line (the upper panel) and the sequencing result (SEQ ID NO: 2) thereof after gene editing mutation (the lower panel).
Figure 1D:
FIGS. 1D to 1G show the expression profiles of the pluripotent stem cell-specific cell markers Oct4, Nanog, Sox2 and SSEA4 of the iPS cell line, respectively.
Figure 1E:
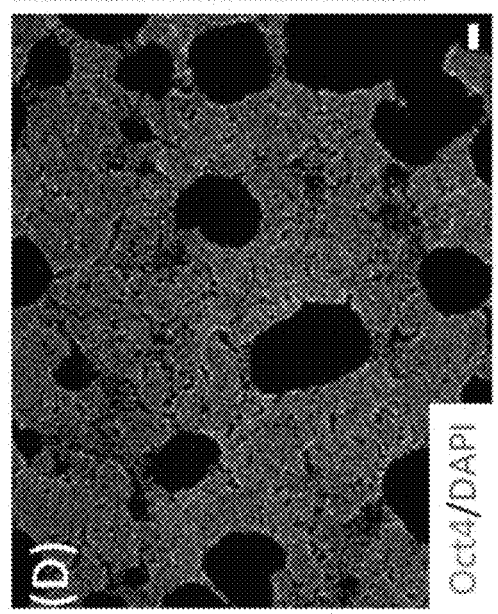
Figure 1F:
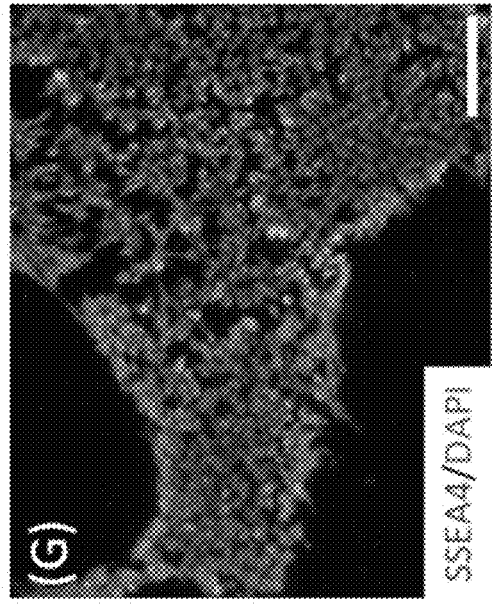
Figure 1G:
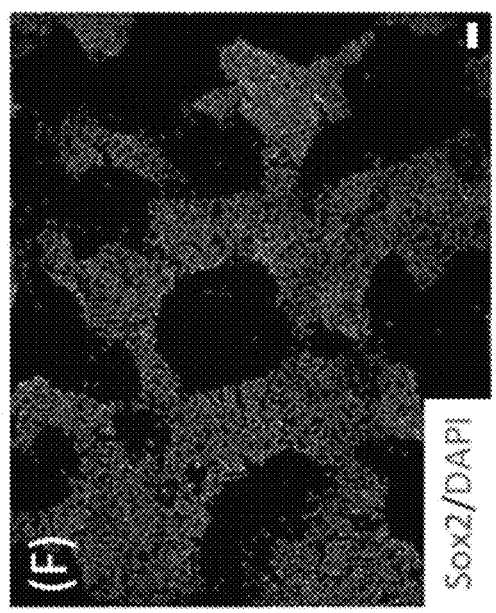
Figures 1H, 1I, 1J:
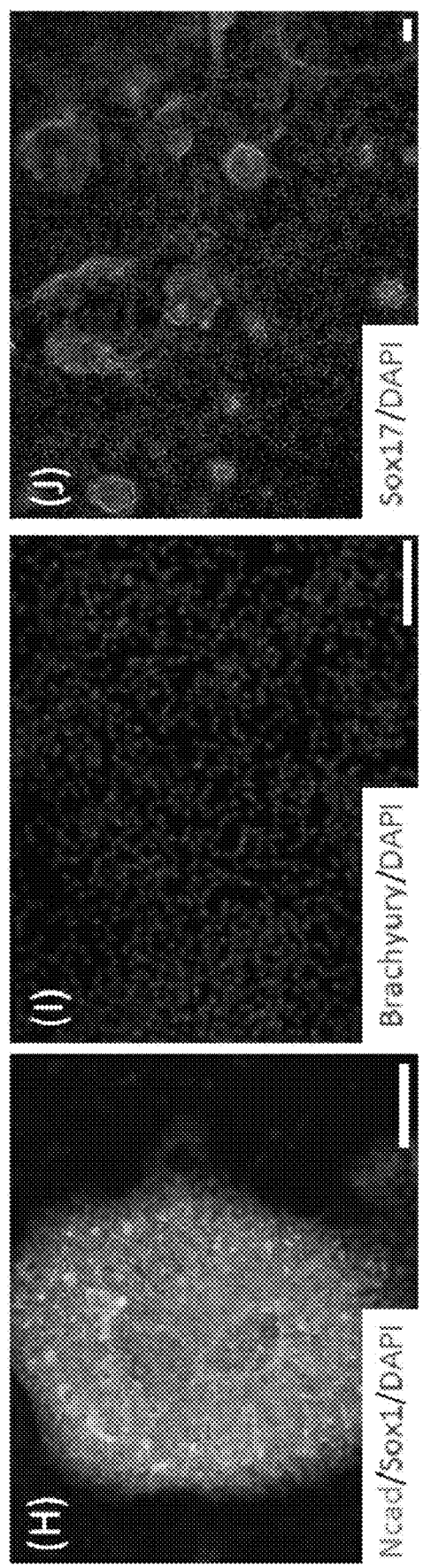
FIGS. 1H to 1J show the expression profiles of the neurorctodermal markers Ncad and Sox1, the mesodermal marker Brachyury and the endodermal marker Sox17 of the iPS cell line, respectively.

Furthermore, in order to be used as a control group for ALS, the point mutations in the SOD1 gene of ALS iPSCs were repaired using a CRISPR/Cas9 gene editing technique. A part of the sequencing results in FIG. 1C showed that the nucleotide at position 256 in the SOD1 gene of ALS iPSCs was mutated from C to G/C (SEQ ID NO: 1) and reversed to C (SEQ ID NO: 2) after the CRISPR editing, and the successful repaired iPSCs are named as SOD1$^{G85G}$ iPSCs.

Example 2: Motor Neuronal Differentiation of ALS iPSCs

The iPSCs used for test were SOD1$^{G85R}$ (ALS) and gene-repaired lines thereof SOD1$^{G85G}$ (healthy), SOD1$^{D90A}$ (ALS) and gene-corrected lines SOD1$^{D90D}$ (healthy), wherein SOD1$^{G85R/G85G}$ iPSCs were established according to Example 1, and SOD1$^{D90A/D90D}$ iPSCs were purchased from WiCell. Through the method of "motor neural differentiation of induced pluripotent stem cells" described above, iPSCs were differentiated into motor neurons which are the dominated lesion cells of ALS and subjected to the immunofluorescent staining assay to analyze specific protein expression as shown in FIGS. 2B to 2N. It was confirmed from the figures that the individual iPS cell line expressed the nerve stem cell-specific proteins, Sox1 and N-cadherin (Ncad), and motor neural stem cell proteins, oligo2 (Olig2) and islet1 (Isl1), at Day 15 of the differentiation, and expressed motor neuron-specific proteins HB9 and neurofilament NF at Day 25 of the differentiation.

Example 3: SOD1$^{G85R/D90A}$ ALS Motor Neurons Exhibited Typical Signs of ALS

Figure 3A:
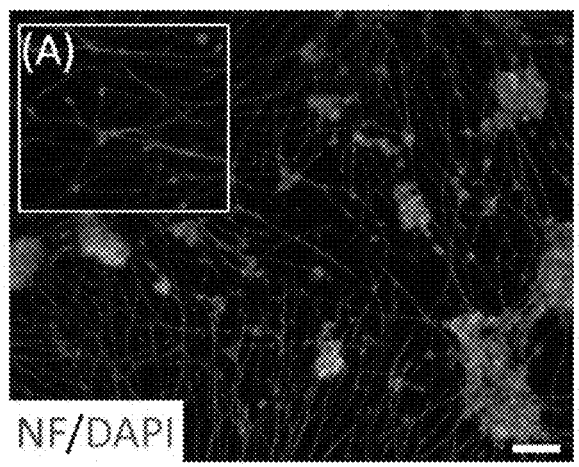
FIG. 3A shows the spherical nerve fiber beads in the SOD1$^{G85R}$ motor neurons.
Figure 3B:
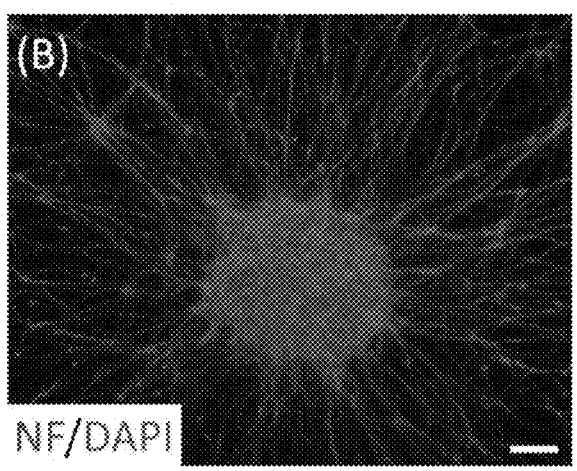
FIG. 3B shows the amount of nerve fibers of an SOD1$^{G85R}$ motor neuron.
Figure 3C:
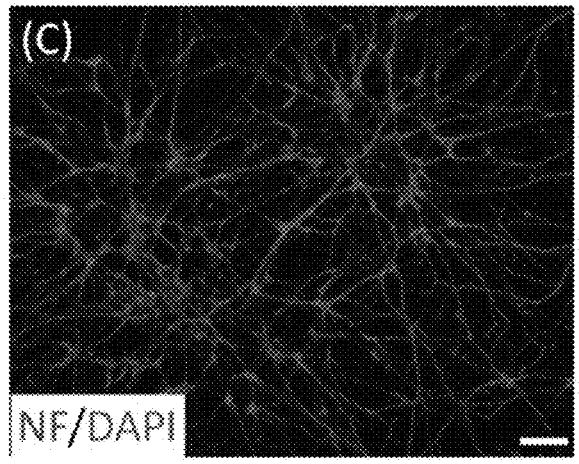
FIG. 3C shows an SOD1$^{G85G}$ motor neuron.
Figure 3D:
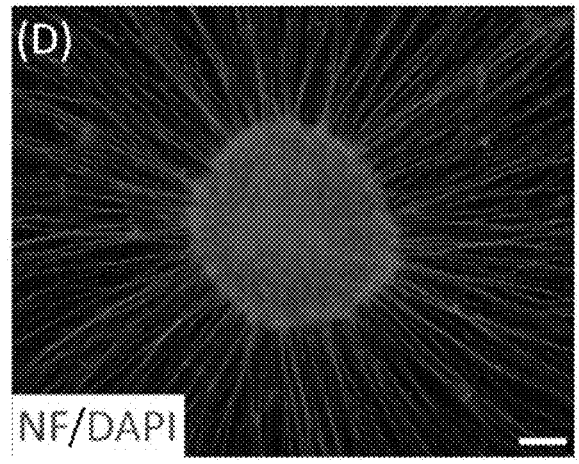
FIG. 3D shows the amount of nerve fibers of an SOD1$^{G85G}$ motor neuron.
Figure 3E:
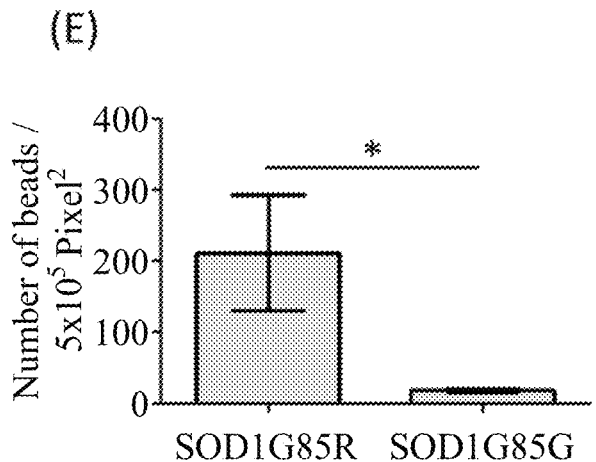
FIGS. 3E and 3F show the spherical tangles in SOD1$^{G85R}$ and SOD1$^{G85G}$ motor neurons and the quantification data of the amount of nerve fibers, respectively.
Figure 3F:
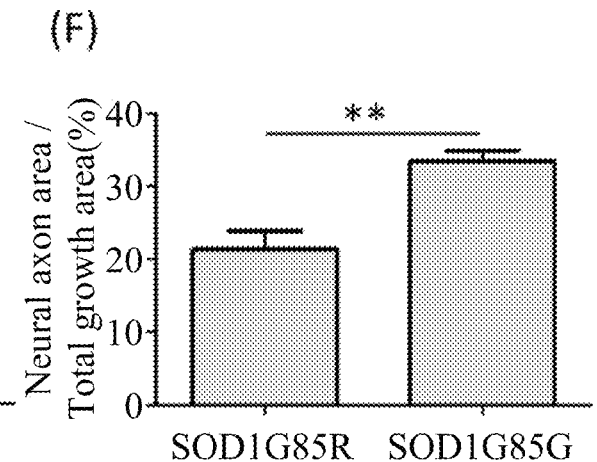
Figure 3G:
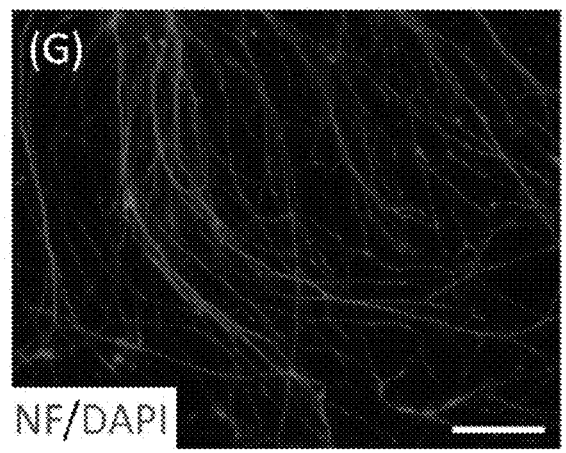
FIG. 3G shows the spherical nerve fiber beads in SOD1$^{D90A}$ motor neurons.
Figure 3H:
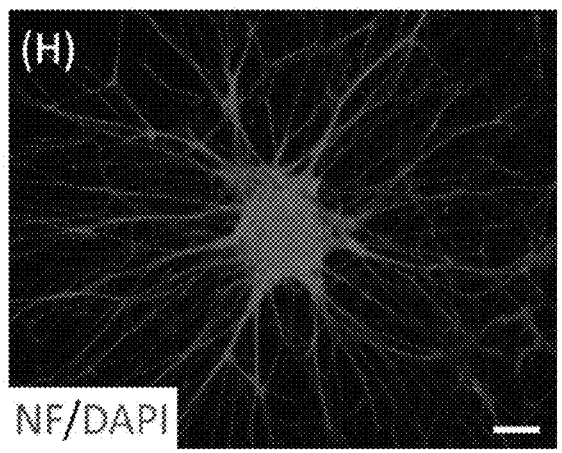
FIG. 3H shows the amount of nerve fibers of an SOD1$^{D90A}$ motor neuron.
Figure 3I:
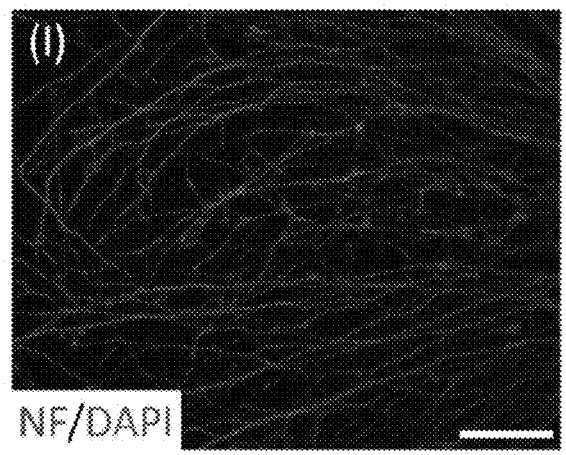
FIG. 3I shows an SOD1$^{D90D}$ motor neuron.
Figure 3J:
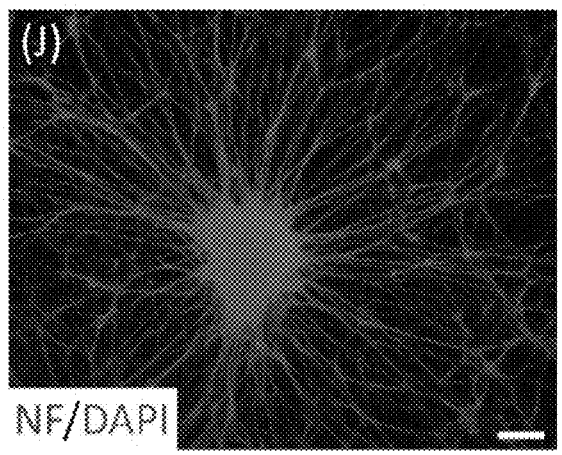
FIG. 3J shows the amount of nerve fibers of an SOD1$^{D90D}$ motor neuron.
Figure 3K:
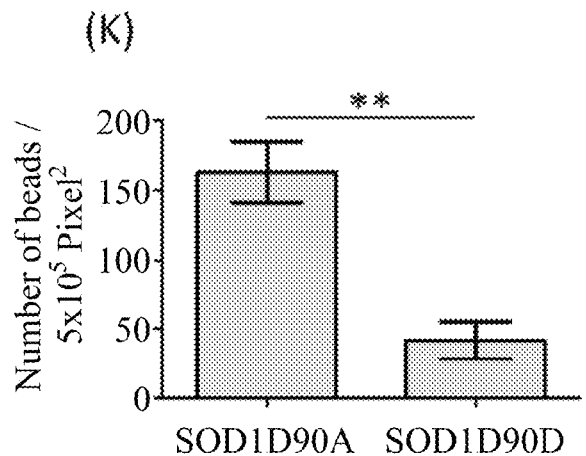
FIGS. 3K and 3L show the spherical tangles in SOD1$^{D90A}$ and SOD1$^{D90D}$ motor neurons and the quantification data of the amount of nerve fibers, respectively.
Figure 3L:
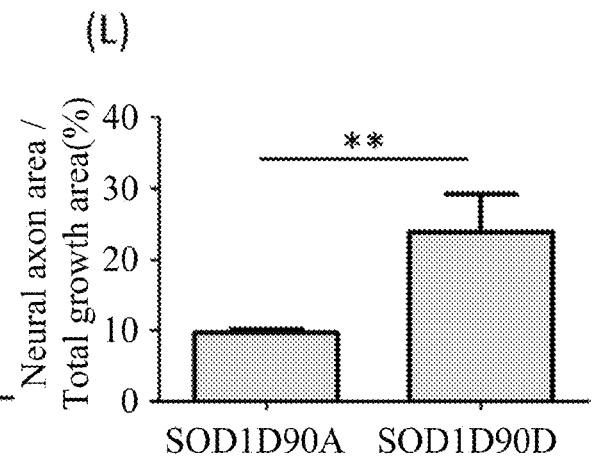

This Example utilized the SOD1$^{G85G/D90D}$ motor neurons differentiated from the iPSCs, in which the pathogenic gene SOD1 had been edited. FIGS. 3A to 3L show the results of NF staining, wherein FIG. 3A and FIG. 3B show the spherical nerve fiber beads and the amount of nerve fibers in an SOD1$^{G85R}$ motor neuron, respectively. FIG. 3C shows an SOD1$^{G85G}$ motor neuron, from which spherical nerve fiber beads were hardly observed, and FIG. 3D shows the amount of nerve fibers in an SOD1$^{G85G}$ motor neuron. Referring to the quantification data of FIG. 3E and FIG. 3F, SOD1$^{G85R}$ ALS motor neurons did generate a higher amount of spherical nerve fiber beads and less nerve fibers than SOD1$^{G85G}$ healthy motor neurons with a significant difference. In another aspect, FIG. 3G and FIG. 3H show the spherical nerve fiber beads and the amount of fibers in an SOD1$^{D90A}$ motor neuron, respectively. FIG. 3I shows an SOD1$^{D90D}$ motor neuron, from which spherical nerve fiber beads were hardly observed, and FIG. 3J shows the amount of fibers in an SOD1$^{D90D}$ motor neuron. Referring to the quantification data of FIG. 3K and FIG. 3L, SOD1$^{D90A}$ ALS motor neurons did generate more spherical nerve fiber beads and less nerve fibers than SOD1$^{D90D}$ healthy motor neurons with a significant difference. These results showed that the motor neurons differentiated from SOD1$^{G85R/D90A}$ iPSCs exhibited two specific atypical signs, i.e., nerve fiber beads and nerve fiber degeneration.

Figure 4A:
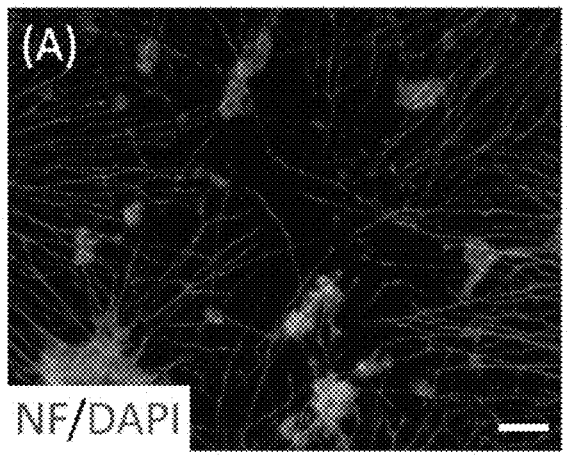
FIG. 4A shows the spherical nerve fiber beads in the SOD1$^{G85R}$ motor neurons.
Figure 4B:
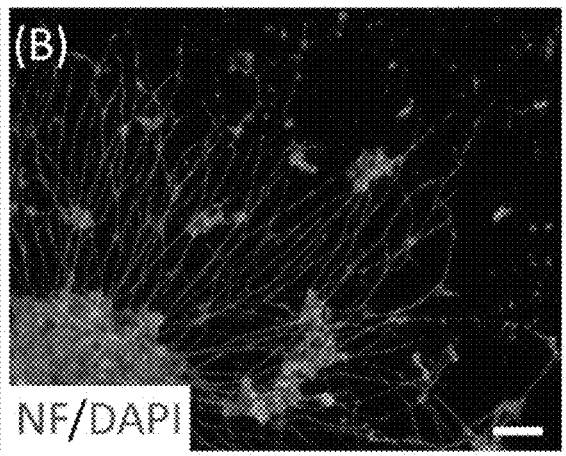
FIG. 4B shows the amount of nerve fibers of SOD1$^{G85R}$ motor neurons.
Figure 4C:
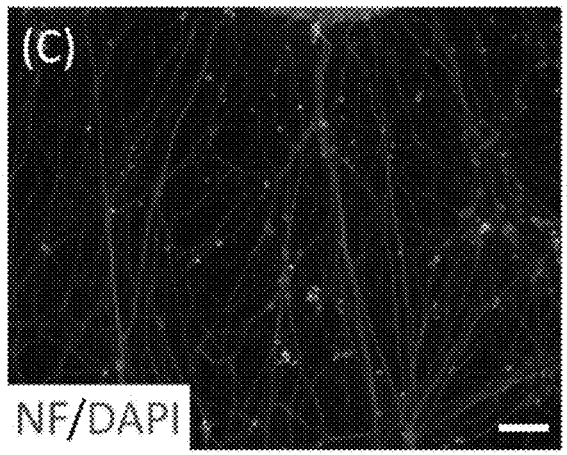
FIG. 4C shows an SOD1$^{G85R}$ motor neuron treated with gastrodin.
Figure 4D:
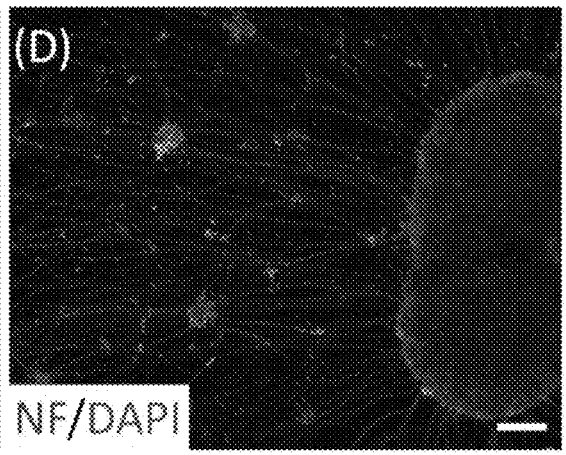
FIG. 4D shows the amount of nerve fibers of an SOD1$^{G85R}$ motor neuron treated with gastrodin.
Figure 4E:
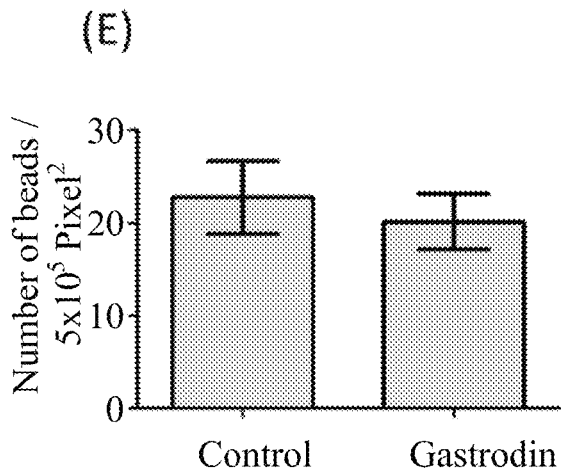
FIGS. 4E and 4F show the spherical tangles in SOD1$^{G85R}$ ALS motor neurons treated or untreated with gastrodin and the quantification data of the amount of nerve fibers, respectively.
Figure 4F:
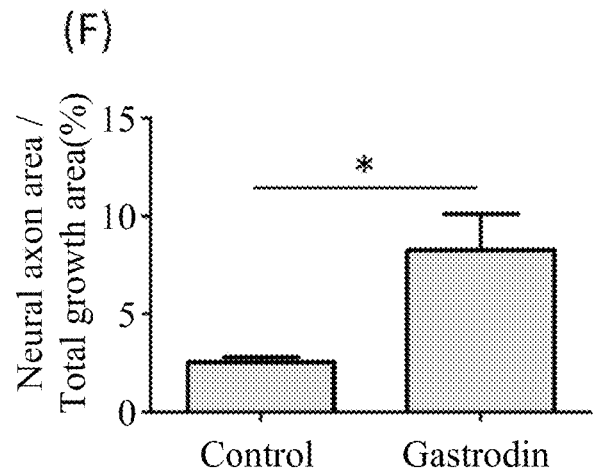
Figure 4G:
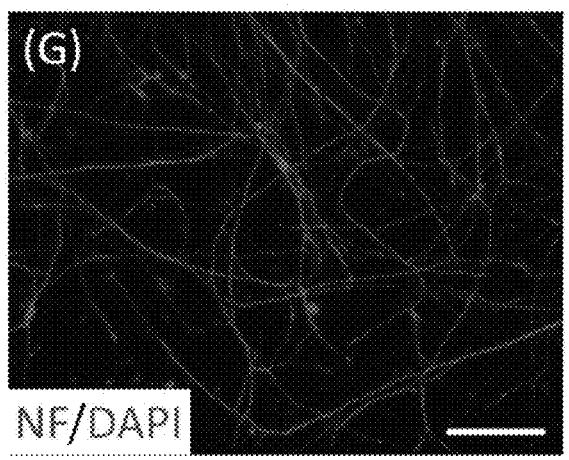
FIG. 4G shows the spherical nerve fiber beads in SOD1$^{D90A}$ motor neurons.
Figure 4H:
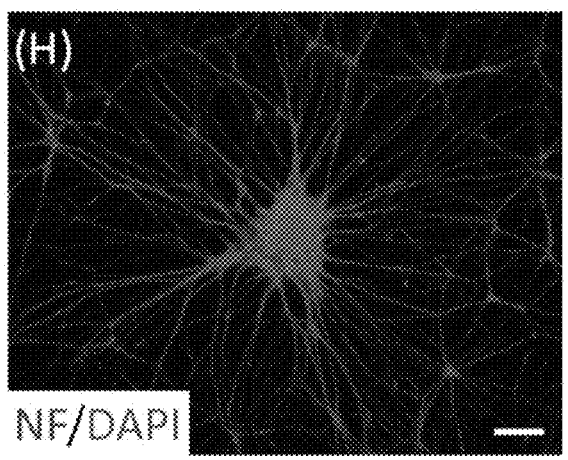
FIG. 4H shows the amount of nerve fibers of an SOD1$^{D90A}$ motor neuron.
Figure 4I:
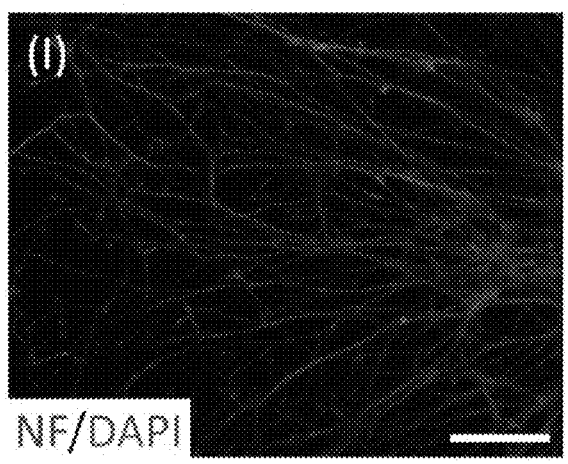
FIG. 4I shows an SOD1$^{D90A}$ motor neuron treated with gastrodin.
Figure 4J:
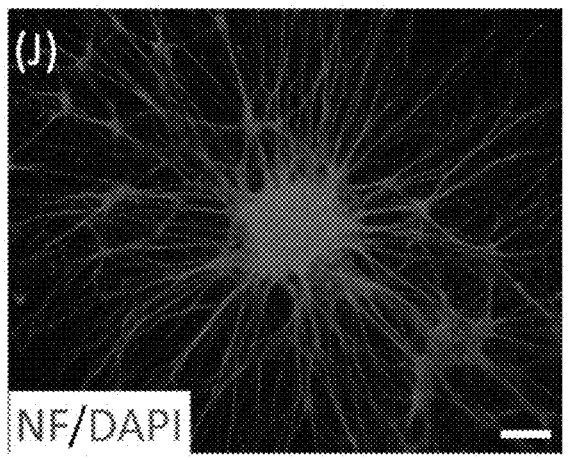
FIG. 4J shows the amount of nerve fibers of an SOD1$^{D90A}$ motor neuron treated with gastrodin.
Figure 4K:
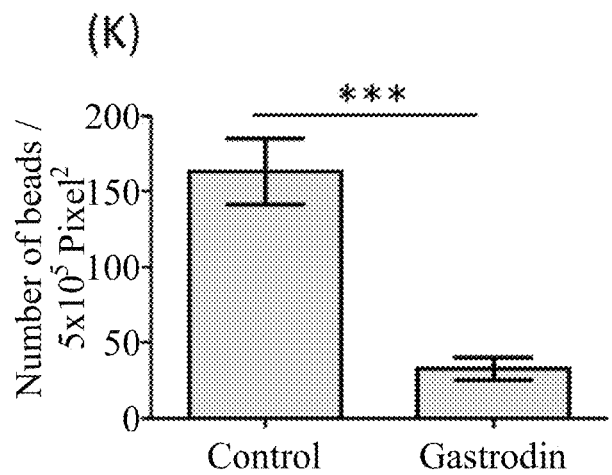
FIGS. 4K and 4L show the spherical tangles in SOD1$^{D90A}$ ALS motor neurons treated or untreated with gastrodin and the quantification data of the amount of nerve fibers, respectively.
Figure 4L:
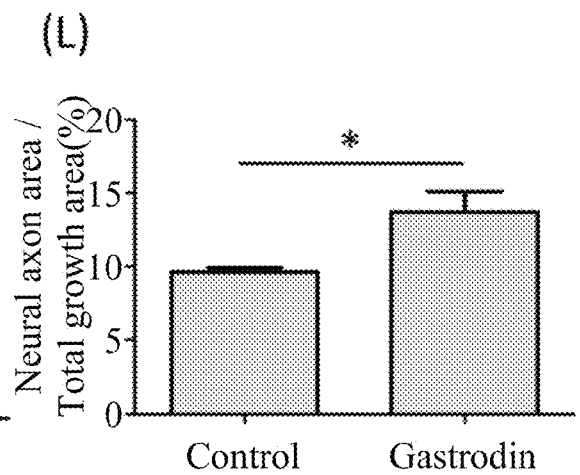

Example 4: Gastrodin Reduced the ALS Signs Exhibited by the SOD1$^{G85R/D90A}$ ALS Motor Neurons In this Example, the motor neurons differentiated from SOD1$^{G85R/D90A}$ ALS iPSCs were treated with 10 μM gastrodin for 72 hrs, and subjected to an NF staining assay to analyze whether the spherical nerve fiber beads thereof were reduced and whether the amount of nerve fibers was improved. FIGS. 4A to 4L show the results of NF staining, wherein FIG. 4A and FIG. 4B show the spherical nerve fiber beads and the amount of fibers in an SOD1$^{G85R}$ motor neuron, respectively. Further, FIG. 4C and FIG. 4D show spherical nerve fiber beads and the amount of fibers in an SOD1$^{G85R}$ motor neuron treated with gastrodin, respectively. As can be clearly seen from the quantification data of FIG. 4E and FIG. 4F, gastrodin can significantly increase the amount of nerve fibers in an SOD1$^{G85R}$ ALS motor neuron. In another aspect, FIG. 4G and FIG. 4H show the spherical nerve fiber beads and the amount of fibers in an SOD1$^{D90A}$ motor neuron, respectively, and FIG. 4I and FIG. 4J show spherical nerve fiber beads and the amount of fibers in an SOD1$^{D90A}$ motor neuron treated with gastrodin. As can be seen from the quantification data of FIG. 4K and FIG. 4L, the spherical nerve fiber beads were significantly decreased, and the amount of nerve fibers was increased in an SOD1$^{D90A}$ ALS motor neuron treated with gastrodin.

Figure 5A:
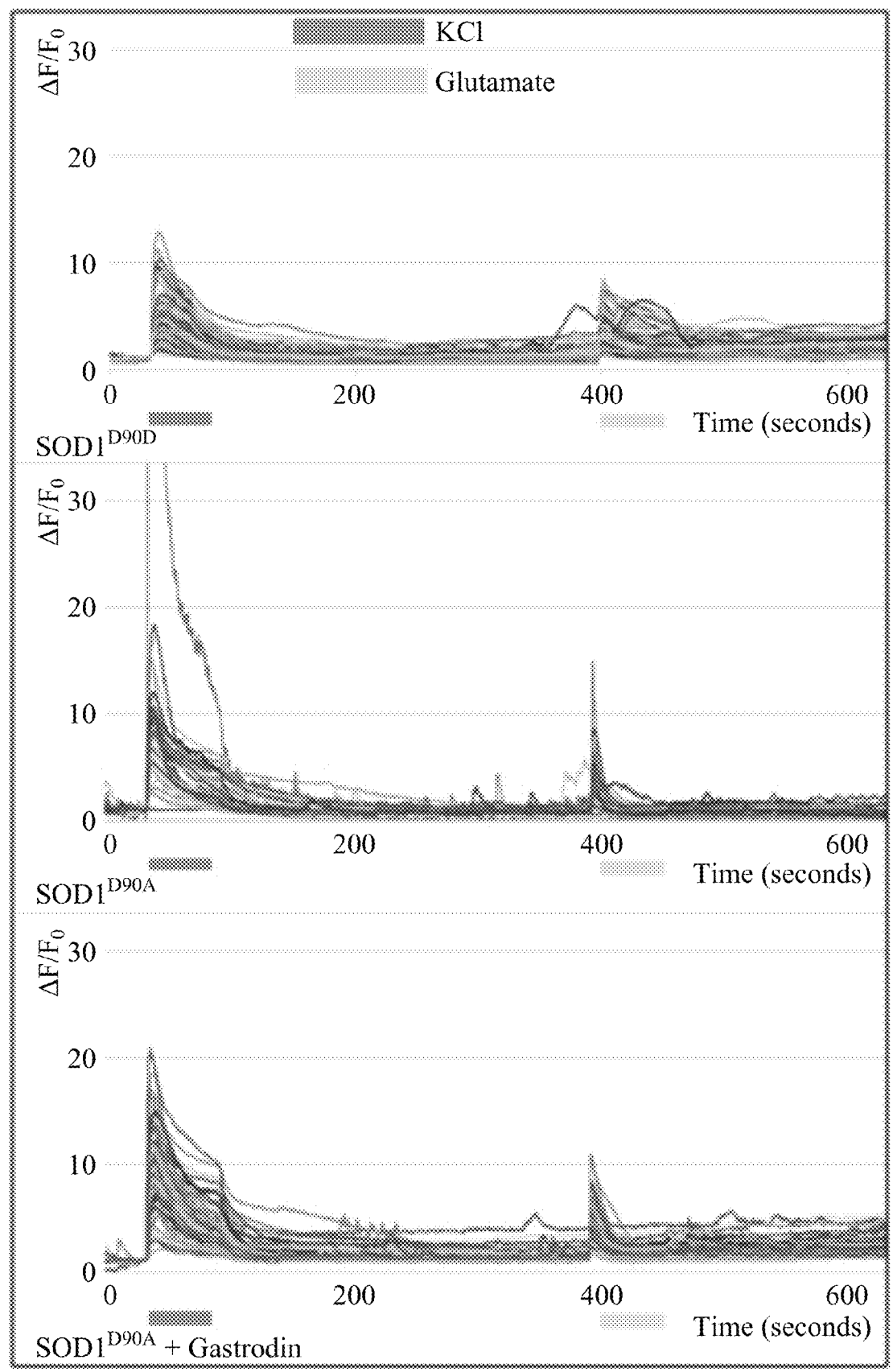
FIGS. 5A to 5E show the calcium ions flow responses of SOD1$^{D90A}$ and SOD1$^{D90D}$ motor neurons as well as SOD1$^{D90A}$ motor neurons treated with gastrodin after stimulation with potassium chloride and glutamate.
Figures 5B, 5C:
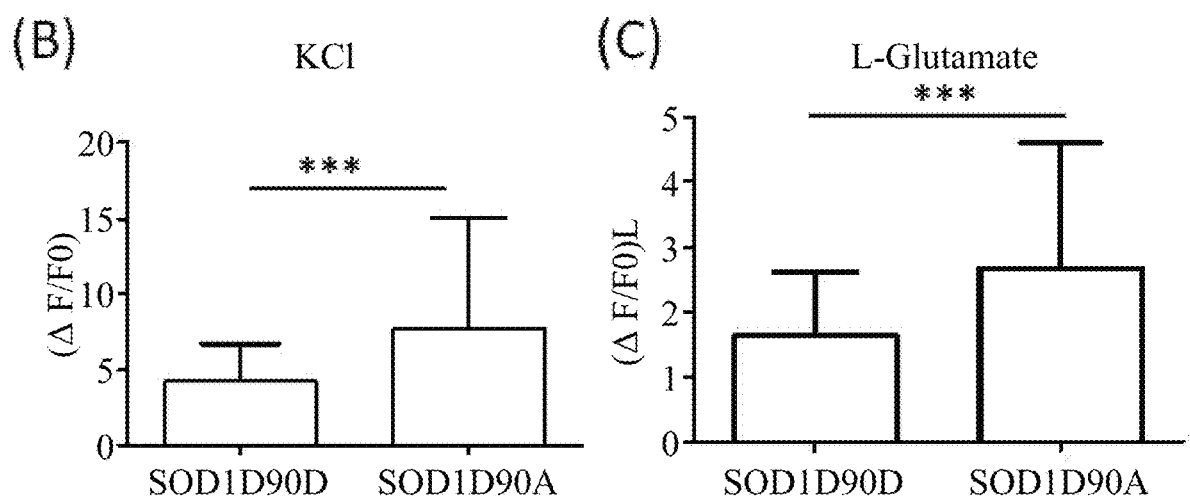
Figures 5D, 5E:
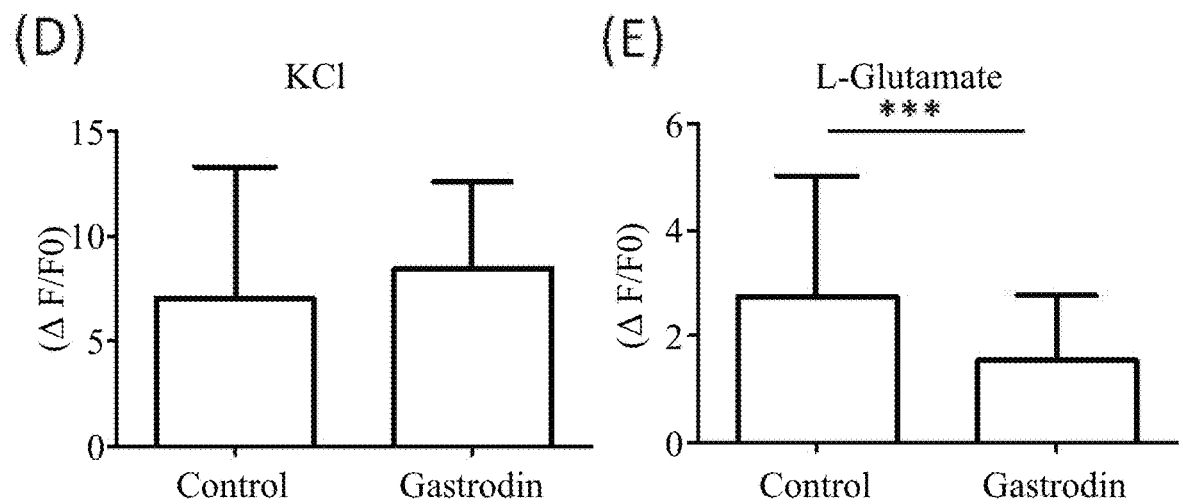

Example 5: Gastrodin Improved the Sign of Neurostimulation Hypersensitivity Exhibited by the Motor Neurons Differentiated from SOD1$^{D90A}$ ALS iPSCs In this Example, SOD1$^{D90A}$, SOD1$^{D90D}$ and gastrodin-treated SOD1$^{D90A}$ motor neurons were stimulated with KCl and glutamate. Changes in calcium ion concentrations were recorded with calcium ion images, and the results were shown in FIGS. 5A to 5E. It can be seen that SOD1$^{D90A}$ ALS motor neurons exhibited stronger calcium ion flow responses to both KCl and glutamate than SOD1$^{D90D}$ healthy motor neurons, which was similar to the properties oversensitive to nerve stimulation in the clinical pathology of ALS (FIG. 5A, FIG. 5B and FIG. 5D). After treatment with gastrodin for 72 hrs, the oversensitive response to glutamate of the SOD1$^{D90A}$ motor neurons was significantly decreased (FIG. 5E).

Figures 6A, 6B:
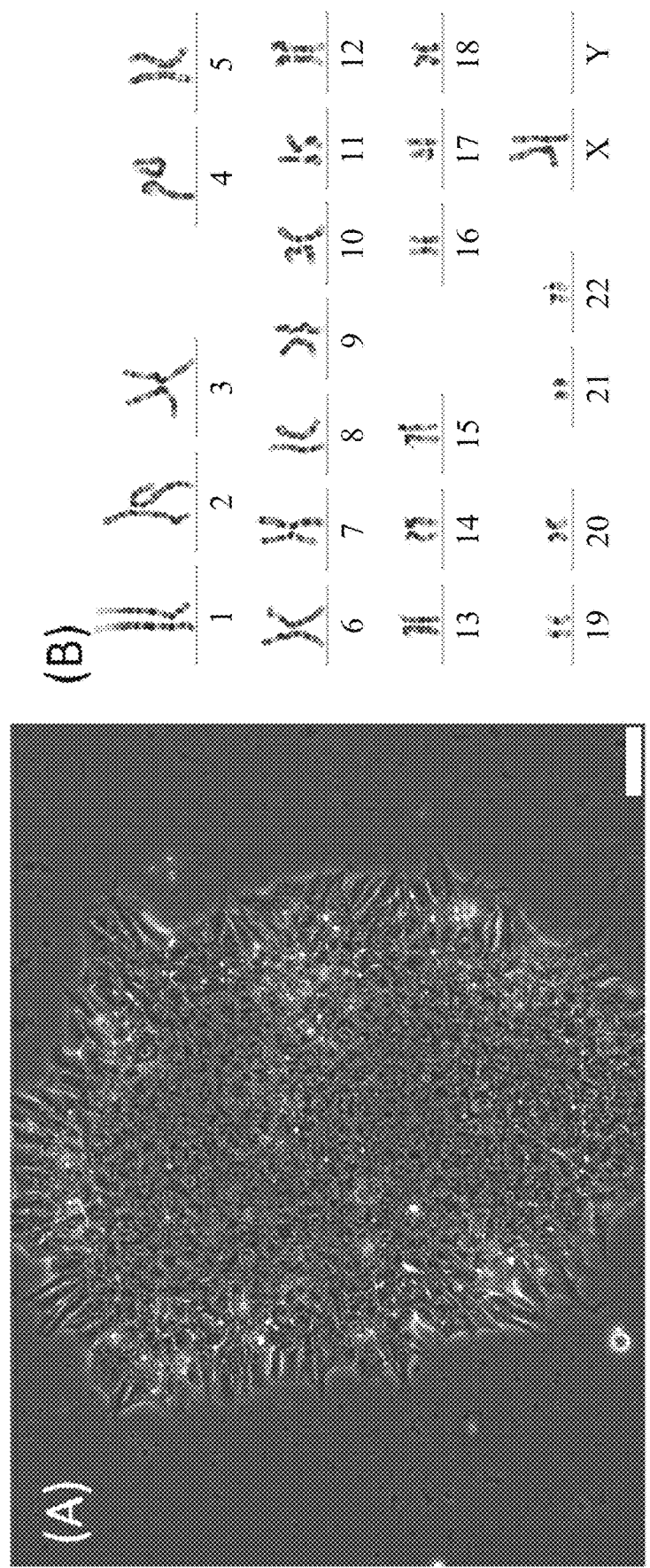
FIG. 6A shows the sALS iPSC cell line established via re-programming from the peripheral blood mononuclear cells of a patient with sporadic ALS (sALS).
FIG. 6B shows the chromosome karyogram of the sALS iPSC cell line.
Figure 6C:
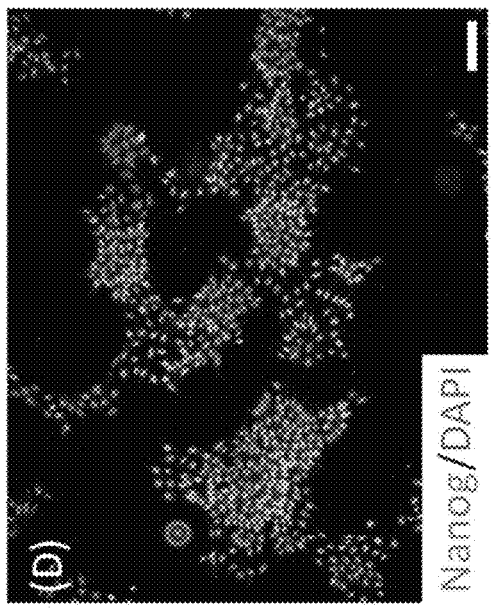
FIGS. 6C to 6F show the expression profiles of pluripotent stem cell-specific makers Oct4, Nanog, Sox2 and SSEA4 of the sALS iPSC cell line, respectively.
Figure 6D:
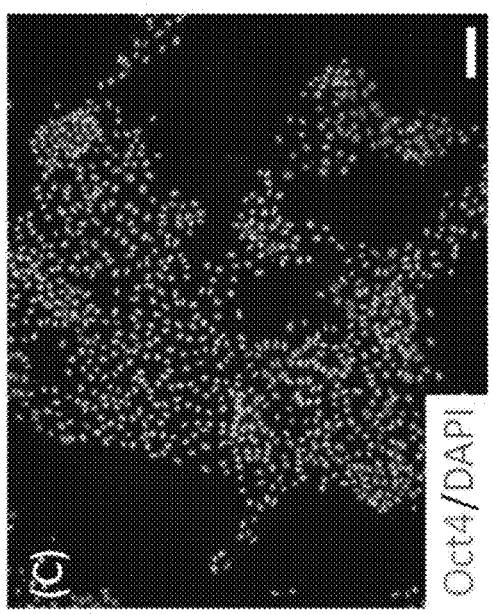
Figure 6E:
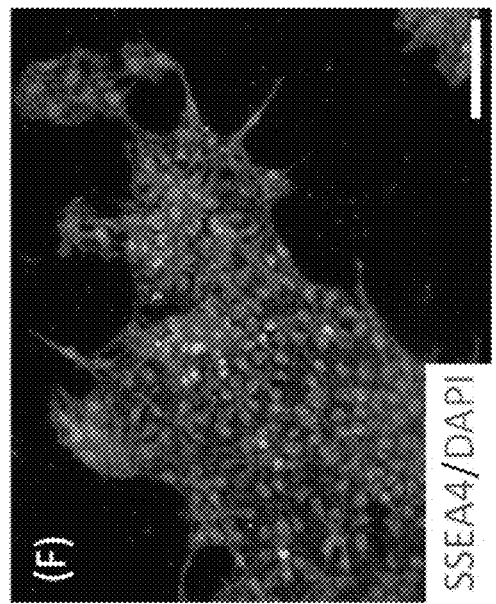
Figure 6F:
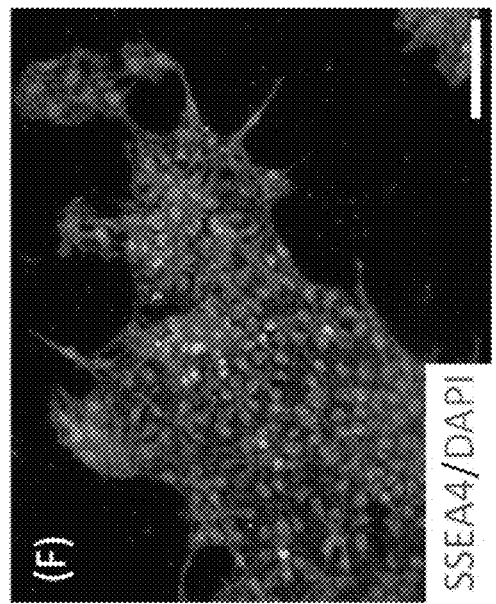

Example 6: Gastrodin Improved the Signs of Neurofibromatosis Exhibited by the Motor Neurons Differentiated from iPSCs of a Sporadic ALS Patient (sALS iPSC)

iPSCs shown in FIG. 6A were established by reprogramming the peripheral blood mononuclear cells of a patient with sporadic ALS (sALS) and subjected to immunofluorescent assay to confirm that the established sALS iPSCs expressed the pluripotent stem cell-specific markers Oct4, Nanog, Sox2 and SSEA4 (FIGS. 6C to 6F). Further, the established sALS iPSCs were tested by the immunofluorescent staining assay to have the ability to differentiate into three types of dermal layers (FIGS. 6G to 6I; neurorctodermal markers: Sox1 and Ncad; mesodermal marker: Brachyury; endodermal marker: Sox17). In addition, as shown in FIG. 6B, the established sALS iPSCs have normal chromosome karyotypes.

Figures 6L, 6M:
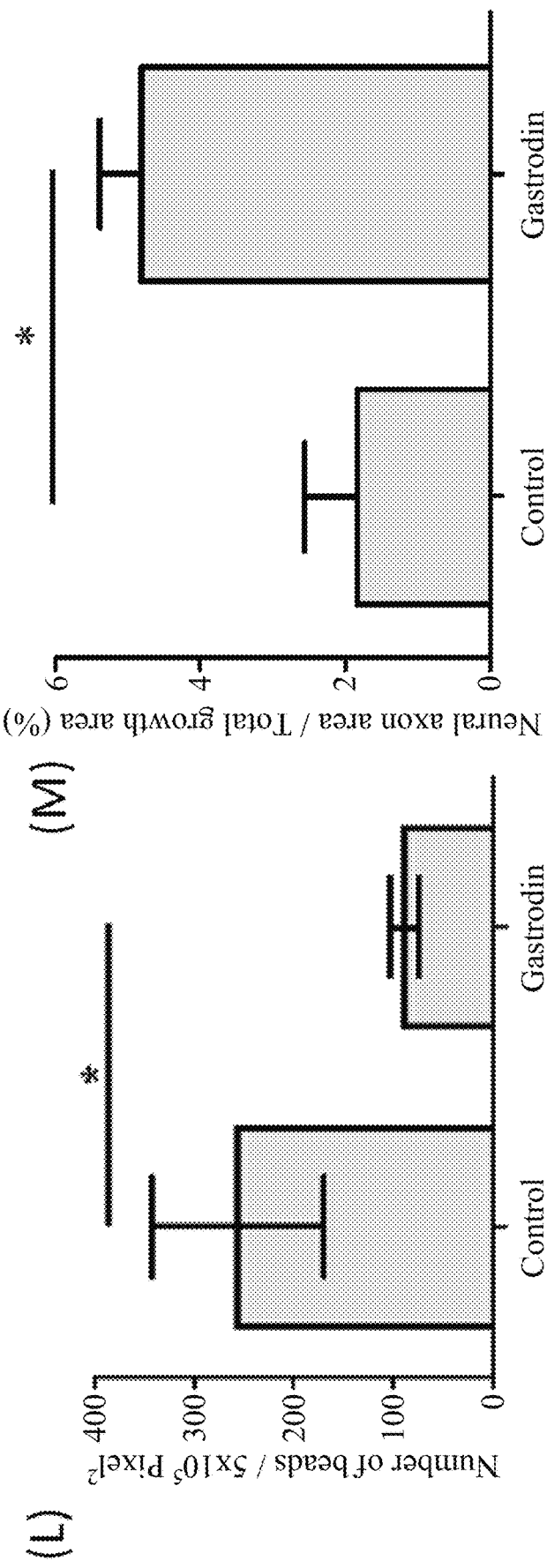
FIGS. 6L and 6M show the reduced spherical nerve fiber beads and increased nerve fibers in the sALS iPSC-differentiated motor neurons treated with gastrodin.

Additionally, a large amount of nerve fiber beads was observed after the differentiation of sALS iPSCs into motor neurons (FIG. 6J and FIG. 6K). The nerve fiber beads were decreased (FIG. 6L) and the amount of nerve fibers was increased (FIG. 6M) after treatment with gastrodin. The result shows that gastrodin has both the therapeutic effect on SOD1 mutant ALS and the improvement in signs of sporadic ALS.

Example 7: Gastrodin Improved Motor Abilities and Motor Functional Indexes of ALS Model Mice and Increased the Survival Time Thereof The Example tested whether gastrodin improved the ALS symptoms of transgenic mice. SOD1$^{G93A}$ transgenic mice began to exhibit degenerative symptoms similar to ALS at about 90 days after birth, including decrease in motor coordination, decrease in motor function index BBB score and decrease in survival time (death occurred at about 120 days after birth).

In this Example, beginning at 60 days after birth, the mice were administered with gastrodin by intraperitoneal injection at a dose of 50 mg/kg or 200 mg/kg for 5 times (with one day interval) every 30 days, until the mice degenerated severely to the extent that the hind lambs lost motor ability completely and until sacrificed. In this Example, motor abilities were tested, and survival time was recorded in days.

Figure 7A:
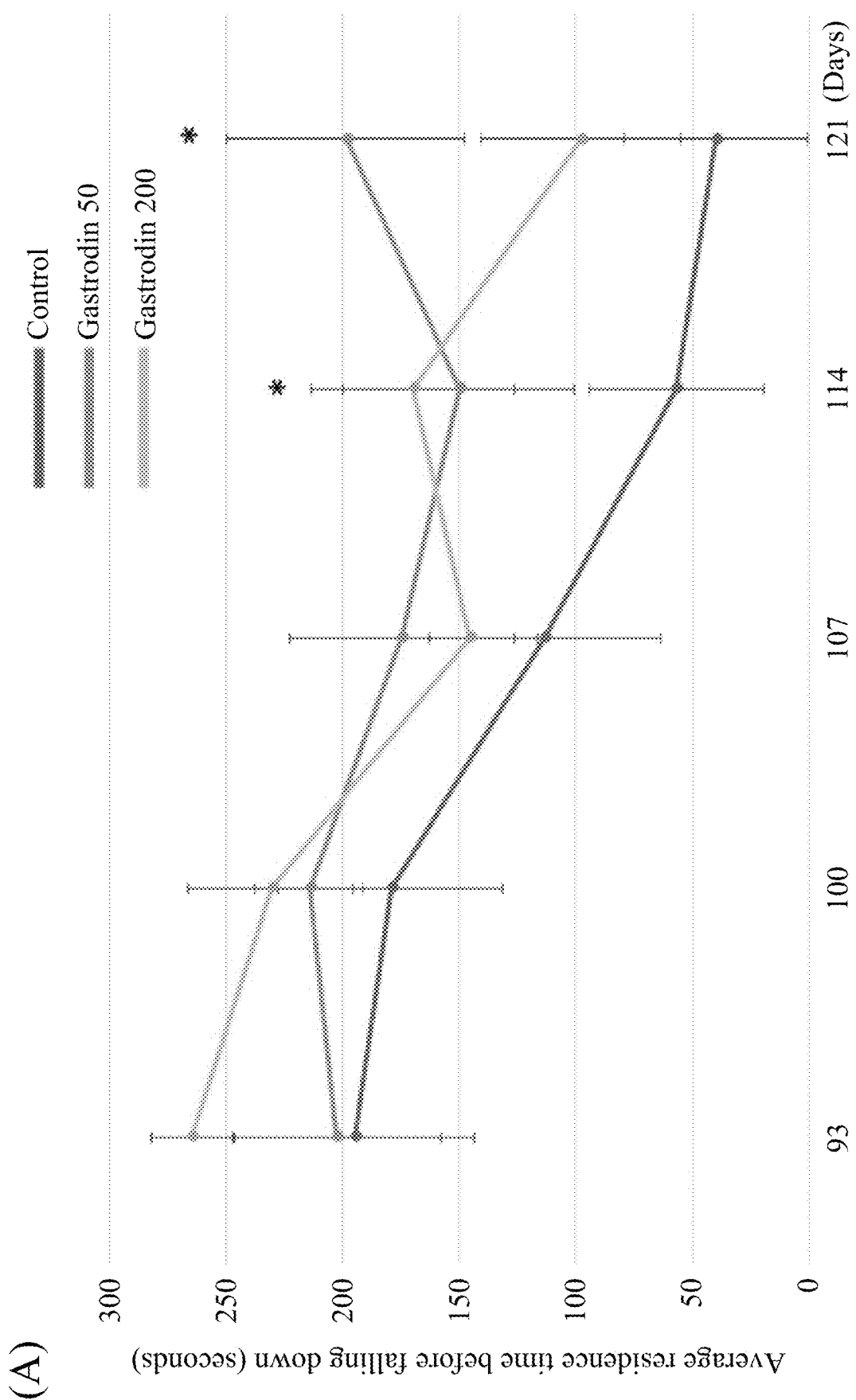
FIGS. 7A to 7C show the roller residence time of the model mice treated with gastrodin at two concentrations (50 mg/kg and 200 mg/kg).
Figure 7B:
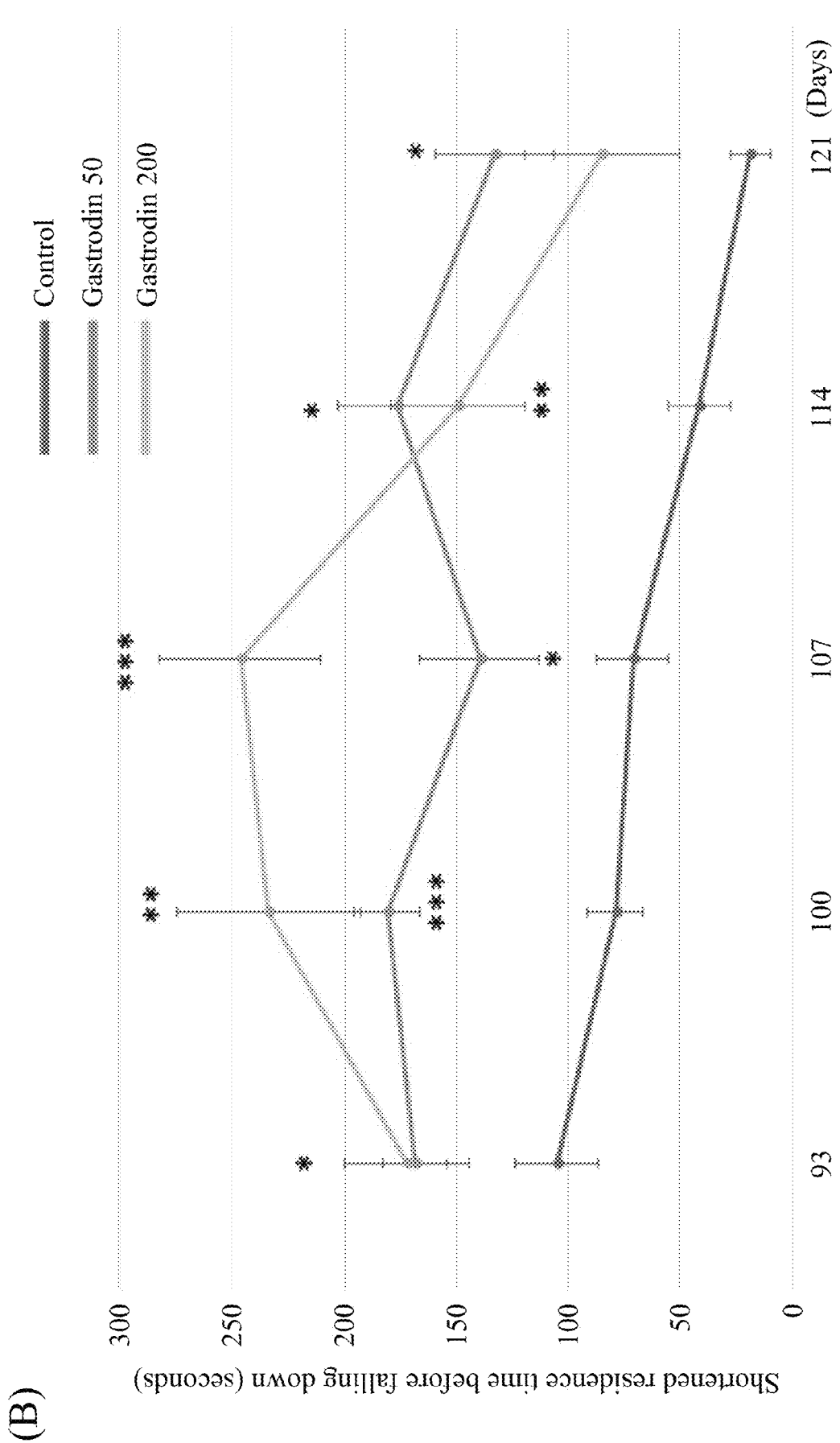
Figure 7C:
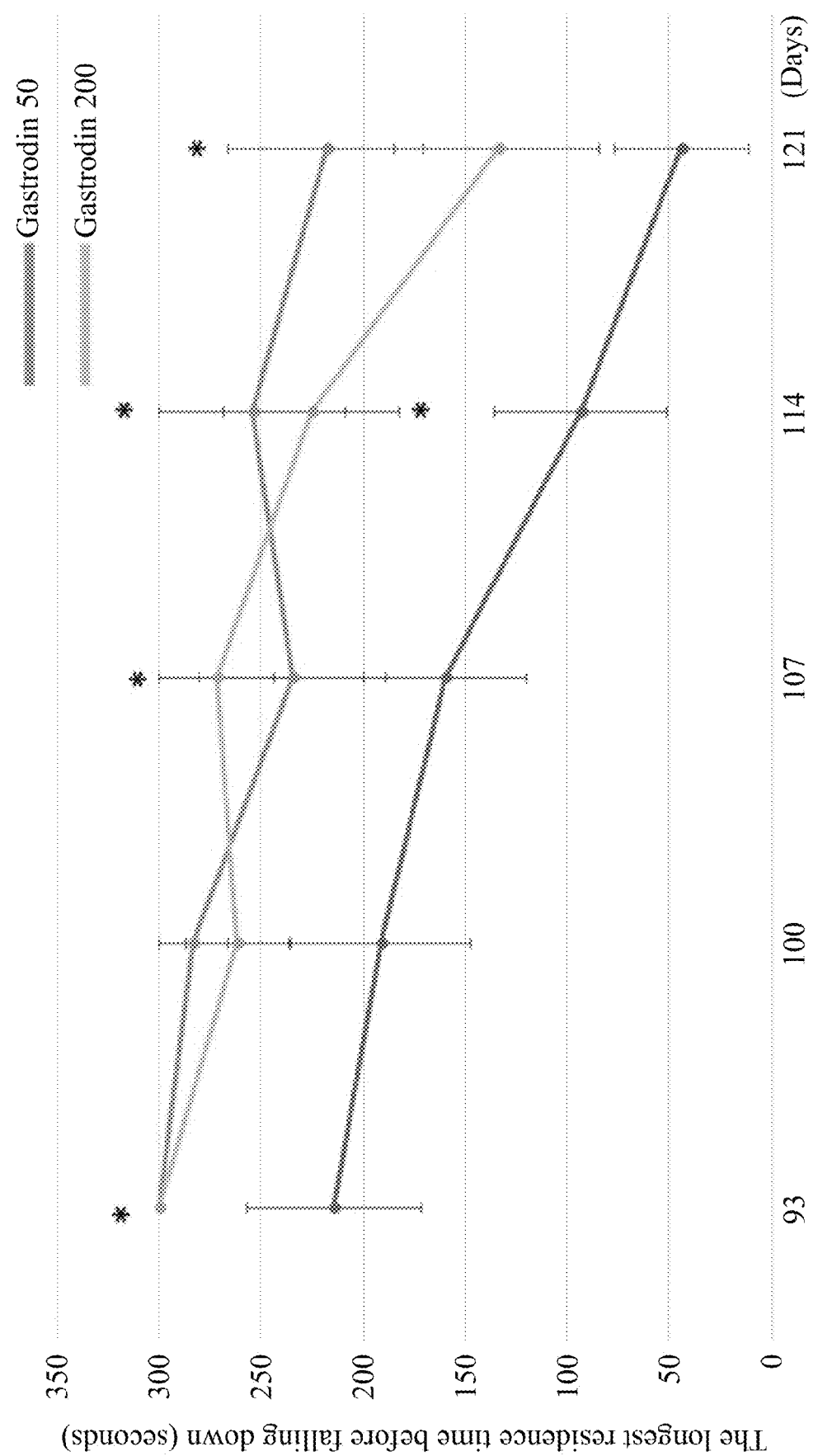
Figure 7D:
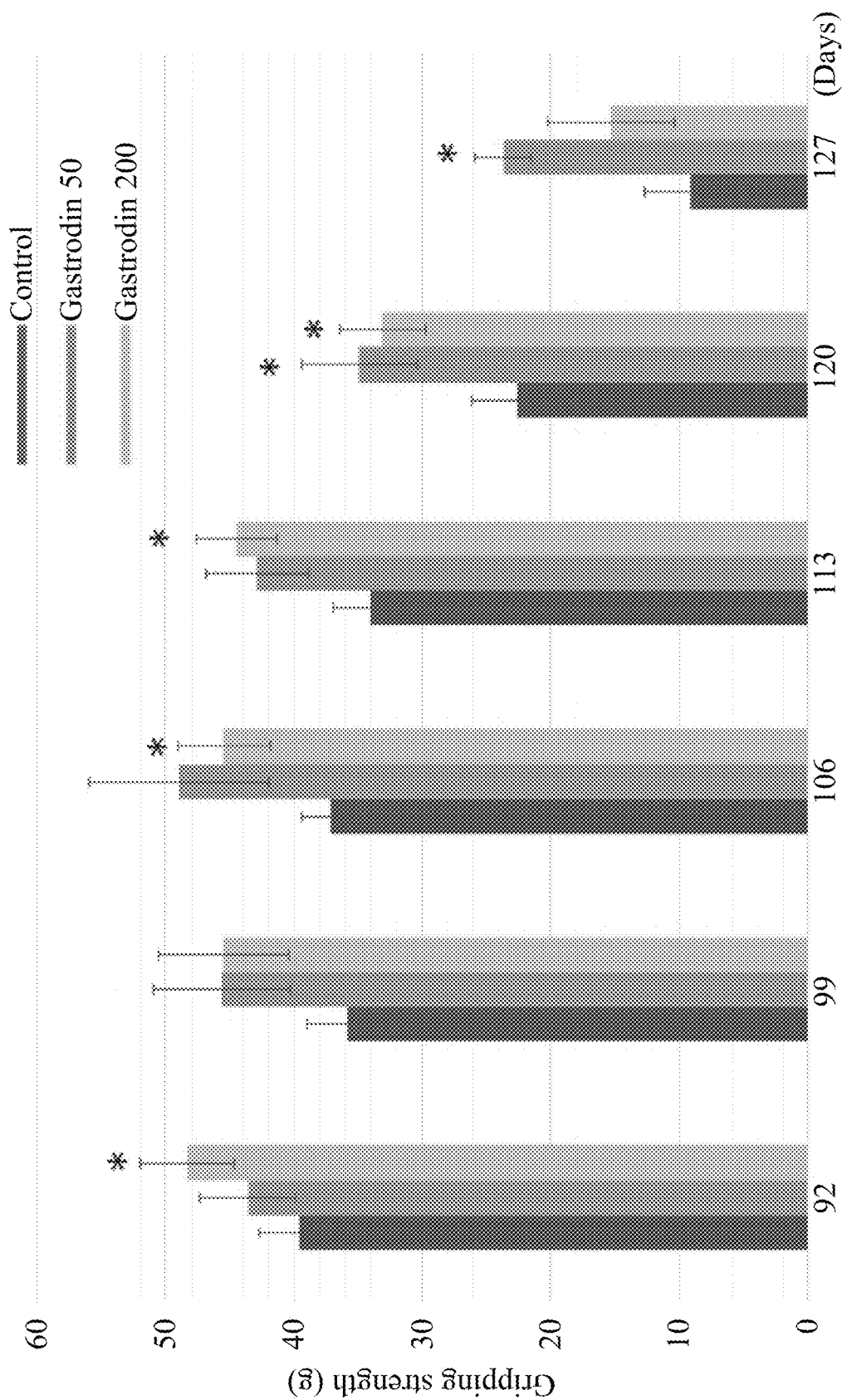
FIG. 7D shows the gripping strength of hind limbs of the model mice on a roller.
Figure 7E:
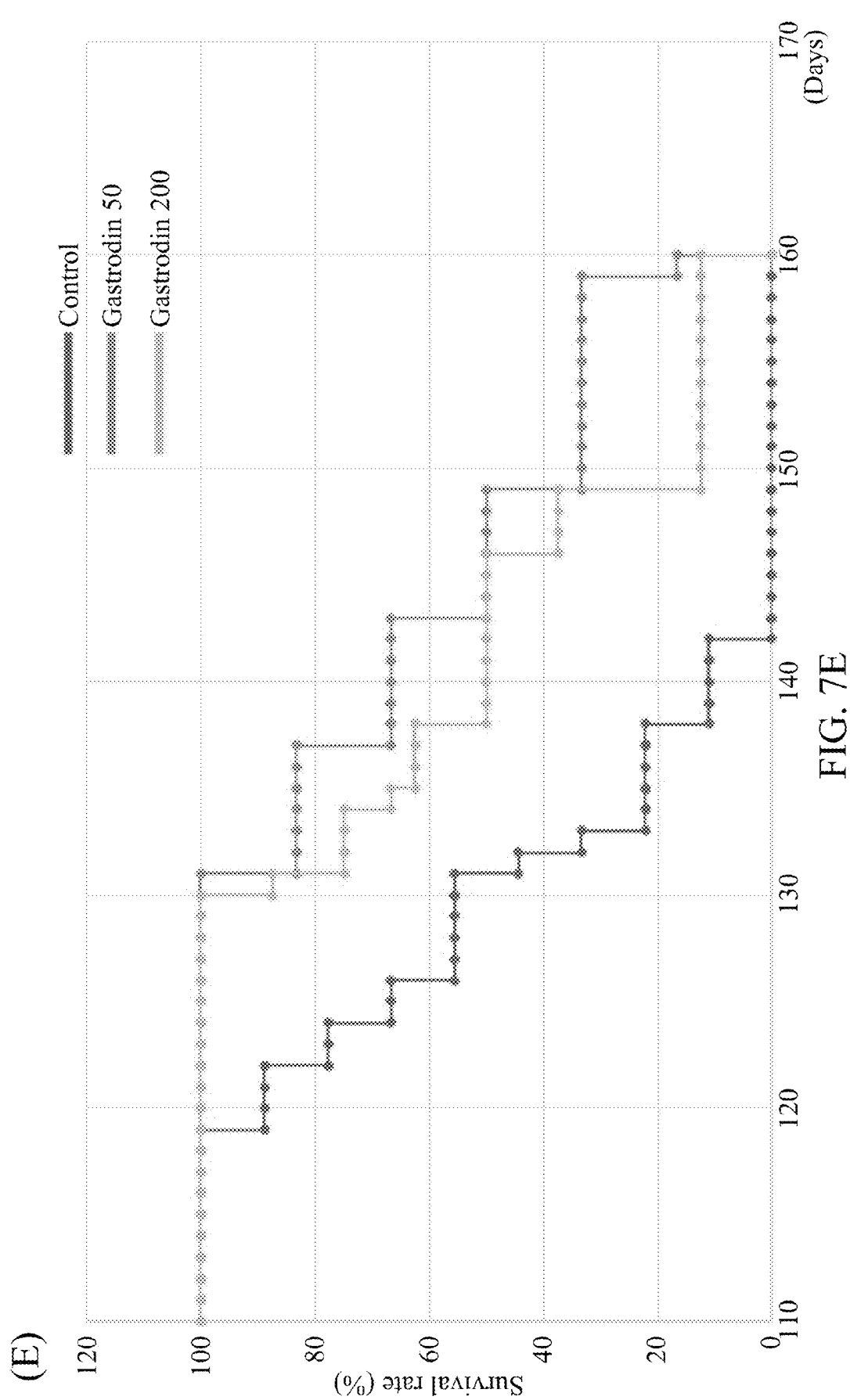
FIGS. 7E and 7F show the survival rates and Basso Beattie Bresnahan (BBB) scores of the model mice treated with gastrodin, respectively.
Figure 7F:
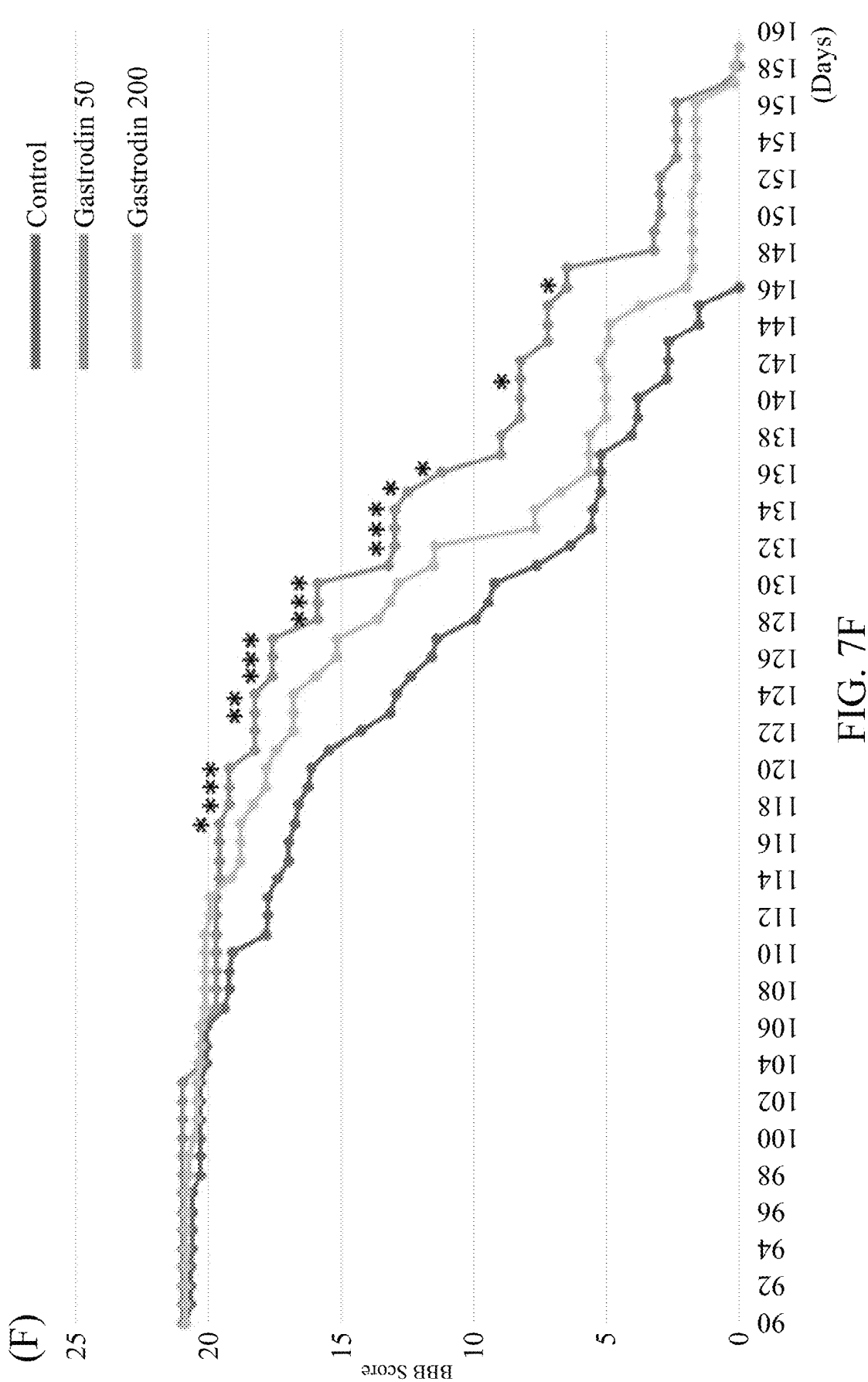

The results were shown in FIGS. 7A to 7E, in which FIGS. 7A to 7C showed that all of the mice administered with gastrodin at the both concentrations exhibited a roller residence time obviously longer than that of the control, and FIG. 7D showed that the gripping strength of the hind limbs was clearly increased after administration of gastrodin. The administration of gastrodin also retarded the decrease in BBB scores of mice (FIG. 7F) and extended the life by about 10 to 20 days (FIG. 7E).

Figure 8A:
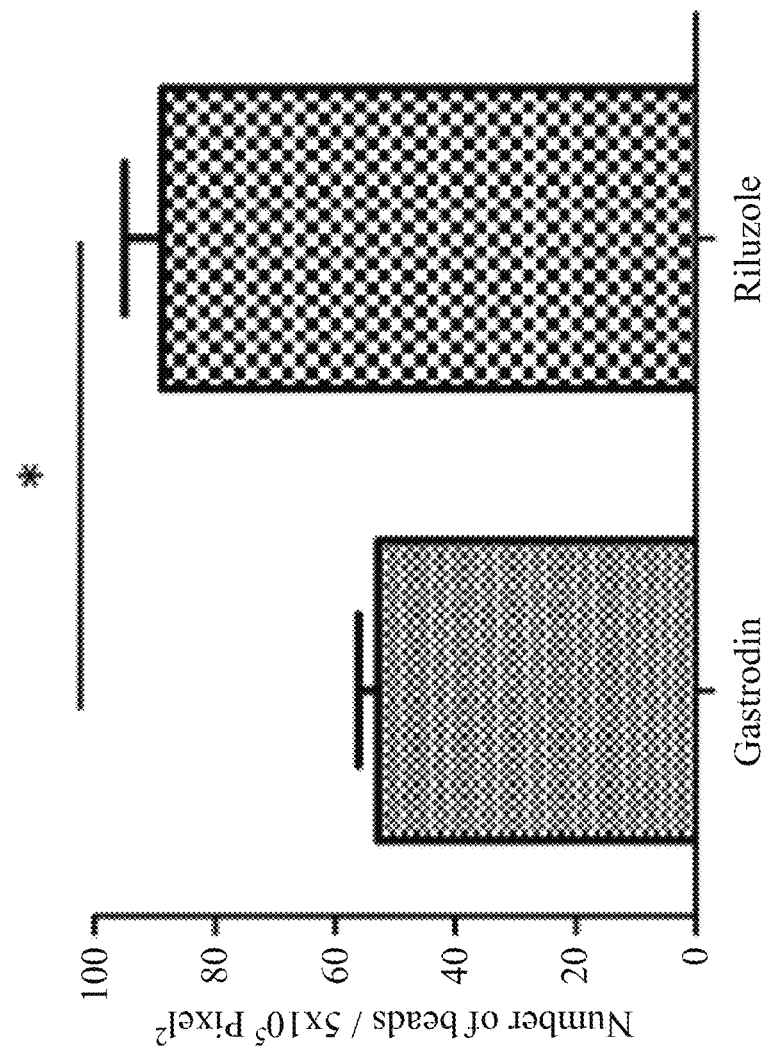
FIGS. 8A and 8B show the comparison of gastrodin and riluzole in reducing the motor neuron symptoms of ALS.
Figure 8B:
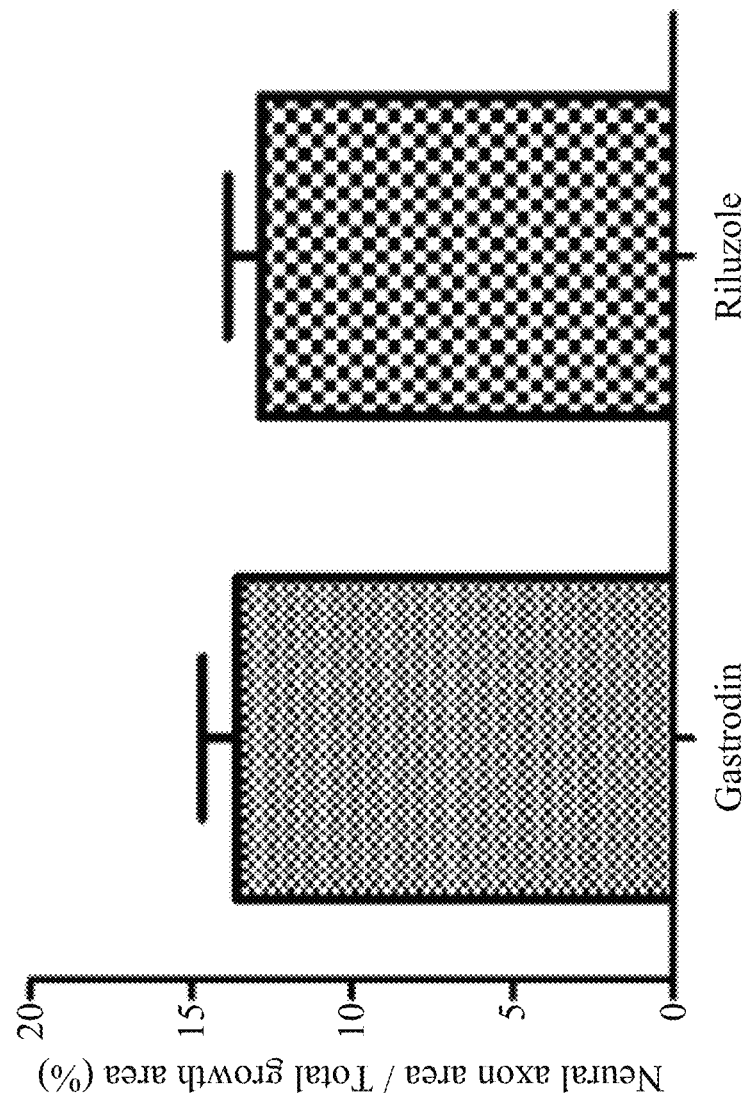

Example 8: Comparison of Gastrodin and the Clinical Medicament for ALS, i.e., Riluzole In this Example, SOD1$^{D90A}$ ALS iPSCs-differentiated motor neurons were used for comparing the efficacies of gastrodin and riluzole on improvement of ALS symptoms. As shown in FIG. 8A and FIG. 8B, gastrodin reduced the spherical nerve fiber beads of SOD1$^{D90A}$ ALS motor neurons by an extent more than riluzole but had an efficacy on increasing number of nerve fibers comparable to riluzole.

The disclosure utilized a human induced pluripotent stem cell technique to reprogram the peripheral blood mononuclear cells of a patient with ALS to iPSCs which differentiated in stages into the lesion cells of ALS, motor neurons, and the motor neurons were found to exhibit typical signs of ALS such as abbreviated as axons, spherical nerve fiber beads, neurofilament accumulation, decreased nerve electrophysiological function, etc.

Increased neural axons and reduced neurofilament accumulation were observed at 72 hrs after addition of gastrodin to the ALS motor neurons and presented significant difference after statistical analysis. Administration of gastrodin promoted the response of ALS motor neurons to KCl, suggesting that it had improvement effects on patient-like signs and neural functions of the ALS motor neurons.

In another aspect, after the injection of gastrodin into the ALS model mice, the loss of motor ability was obviously delayed; for example, the BBB score was responsive, and the roller residence time and the gripping strength of claws were increased. Also, the symptoms at an earlier stage were delayed, and the mortality rate was reduced. In addition, the overall survival time was increased by 10 days, and the suppression on loss of active ability was improved by about 20 days when comparing to the control group.

What is claimed is:

1. A method for relieving amyotrophic lateral sclerosis in a subject in need thereof, comprising:
    administering, to the subject, a pharmaceutical composition comprising a therapeutically effective dose of gastrodin and a pharmaceutically acceptable carrier, wherein the subject has at least one disease selected from the group consisting of hereditary amyotrophic lateral sclerosis and sporadic amyotrophic lateral sclerosis wherein the gastrodin has at least one effect observed in an analysis on the subject selected from the group consisting of improvement in axon growth of neurons, decrease in accumulation of neurofilaments, and recovery of nerve electrophysiological function, as compared to those of a subject that has not been administered with the therapeutically effective dose of gastrodin.

2. The method of claim 1, wherein the gastrodin is administered to the subject at a therapeutically effective dose from about 1 mg/kg body weight to about 1,000 mg/kg body weight per day.

3. The method of claim 2, wherein the gastrodin is administered to the subject at a therapeutically effective dose from about 10 mg/kg body weight to about 500 mg/kg body weight per day.

4. The method of claim 3, wherein the gastrodin is administered to the subject at a therapeutically effective dose from about 30 mg/kg body weight to about 250 mg/kg body weight per day.

5. The method of claim 1, wherein the subject has at least one amino acid mutation in superoxide dismutase 1 gene.

6. The method of claim 1, wherein the gastrodin is administered to the subject over a period of 1 month to 3 years.

7. The method of claim 1, wherein the pharmaceutical composition is administered to the subject by at least one route selected from the group consisting of corticospinal, intrathecal, intracerebral, intravenous, intraperitoneal, and subcutaneous injection.

8. The method of claim 1, further comprising administering at least one additional therapy for amyotrophic lateral sclerosis to the subject.

9. The method of claim 8, wherein the additional therapy for amyotrophic lateral sclerosis is administration of at least one medicament selected from the group consisting of riluzole, edaravone and creatine.

* * * * *